United States Patent
Hamblin et al.

(10) Patent No.: US 8,735,390 B2
(45) Date of Patent: *May 27, 2014

(54) POLYMORPHS AND SALTS

(75) Inventors: Julie Nicole Hamblin, Stevenage (GB); Paul Spencer Jones, Stevenage (GB); Suzanne Elaine Keeling, Stevenage (GB); Joelle Le, Stevenage (GB); Charlotte Jane Mitchell, Stevenage (GB); Nigel James Parr, Stevenage (GB); Robert David Willacy, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/821,585

(22) PCT Filed: Sep. 6, 2011

(86) PCT No.: PCT/EP2011/065419
§ 371 (c)(1),
(2), (4) Date: Mar. 8, 2013

(87) PCT Pub. No.: WO2012/032067
PCT Pub. Date: Mar. 15, 2012

(65) Prior Publication Data
US 2013/0165441 A1    Jun. 27, 2013

Related U.S. Application Data

(60) Provisional application No. 61/380,748, filed on Sep. 8, 2010.

(51) Int. Cl.
*A61K 31/5377* (2006.01)
*C07D 413/14* (2006.01)

(52) U.S. Cl.
CPC .......... *A61K 31/5377* (2013.01); *C07D 413/14* (2013.01)
USPC ....................................... 514/234.5; 544/131

(58) Field of Classification Search
CPC ......................... A61K 31/5377; C07D 413/14
USPC ....................................... 544/131; 514/234.5
See application file for complete search history.

(56) References Cited

U.S. PATENT DOCUMENTS

2010/0280029 A1* 11/2010 Hamblin et al. ........... 514/234.5

FOREIGN PATENT DOCUMENTS

WO    2010/125082 A1    11/2010

OTHER PUBLICATIONS

Cancer and Metastasis Reviews (1998), 17(1), 91-106.*
Science (1999), vol. 286, 531-537.*
Voskoglou-Nomikos et al., Clinical Cancer Research, vol. 9, 4227-4239, 2003.*
ptcl.chem.ox.ac.uk/MSDS structure activity relationship; Jaworska, 1-8, 2004.*
Berge et al., Journal of Pharmaceutical Sciences, vol. 66, No. 1, Jan. 1977, pp. 1-19.*
Verheijen, et al.; "Phosphatidylinositol 3-kinase (PI3K) inhibitors as anticancer drugs"; Jun. 1, 2007; Drugs of the Future, Prous Science, ES.; vol. 32(6); pp. 537-547.

* cited by examiner

*Primary Examiner* — Rebecca Anderson
(74) *Attorney, Agent, or Firm* — Robert J. Smith

(57) ABSTRACT

The present invention is directed to novel polymorphs and salts of a compound which is an inhibitor of kinase activity.

3 Claims, 3 Drawing Sheets

POLYMORPHS AND SALTS

CROSS-REFERENCE TO RELATED APPLICATIONS

This application is filed pursuant to 35 U.S.C. §371 as a United States National Phase Application of International Application No. PCT/EP2011/065419 filed Sep. 6, 2011 which claims priority from U.S. Provisional Application No. 61/380,748 files Sep. 8, 2010.

FIELD OF THE INVENTION

The present invention is directed to novel polymorphs and salts of a compound which is an inhibitor of kinase activity, more specifically a compound which is an inhibitor of the activity or function of phosphoinositide 3'OH kinase isoform delta (hereinafter PI3Kδ), processes for their preparation, pharmaceutical compositions comprising them, and their use in the treatment of various disorders.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3Kδ) generate second messengers from the membrane phospholipid pools. Class I PI3Ks convert the membrane phospholipid PI(4,5)$P_2$ into PI(3,4,5)$P_3$, which functions as a second messenger. PI and PI(4)P are also substrates of PI3K and can be phosphorylated and converted into PI3P and PI(3,4)$P_2$, respectively. In addition, these phosphoinositides can be converted into other phosphoinositides by 5'-specific and 3'-specific phophatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life. Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class O PI3Ks can phosphorylate phosphatidylinositol (PI), phosphatidylinositol-4-phosphate (PI4P), and phosphatidylinositol-4,5-bisphosphate (PI(4,5)$P_2$) to produce phosphatidylinositol-3-phosphate (PI3P), phosphatidylinositol-3,4-bisphosphate (PI(3,4)$P_2$), and phosphatidylinositol-3,4,5-trisphosphate (PI(3,4,5)$P_3$, respectively. Class II PI3Ks can phosphorylate PI and PI4P. Class III PI3Ks can only phosphorylate PI (Vanhaesebroeck et al. (1997), above; Vanhaesebroeck et al. Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of PI(4,5)$P_2$ to PI(3,4,5)$P_3$

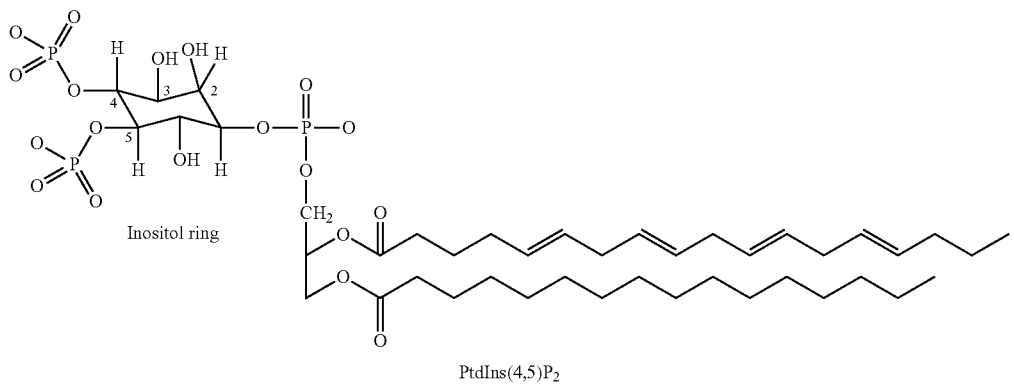

PtdIns(4,5)$P_2$

↓ PI3K

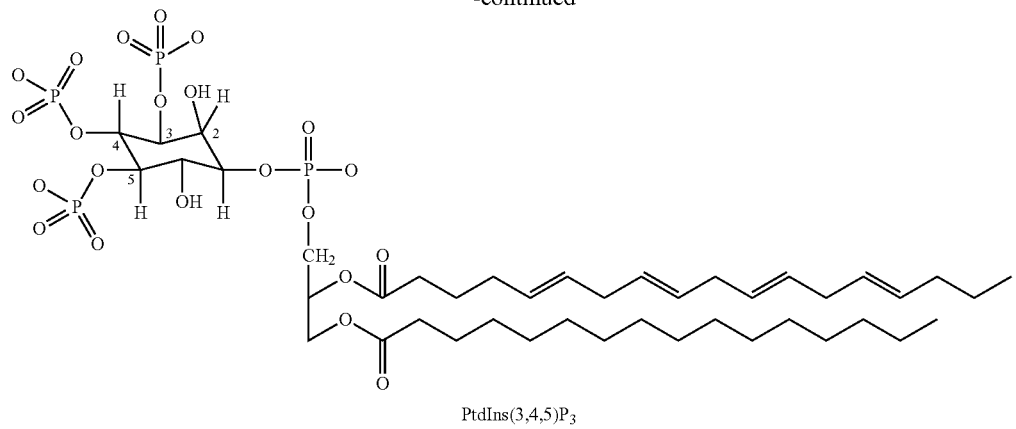

PtdIns(3,4,5)P$_3$

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3) P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, which have been shown to be capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation, is believed to be involved in a wide range of cellular responses including cell growth, differentiation, and apoptosis (Parker, Current Biology 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pages et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)). PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 μM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

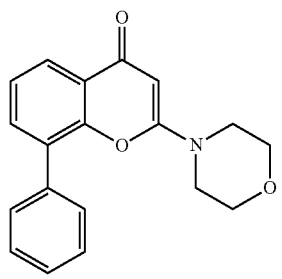

LY294002

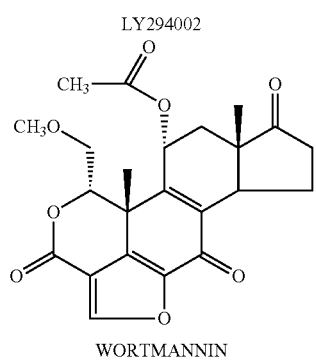

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins (3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5) P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the P3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonists (LABA) in asthma.

In the vasculature, P3Kδ is expressed by endothelial cells and participates in neutrophil trafficking by modulating the proadhesive state of these cells in response to TNFalpha (Puri et al. Blood (2004) 103(9) p. 3448-56.). A role for P3Kδ in TNFalpha-induced signalling of endothelial cells is demonstrated by the pharmacological inhibition of Akt phosphorylation and PDK1 activity. In addition, P3Kδ is implicated in vascular permeability and airway tissue edema through the VEGF pathway (Lee et al. J. Allergy Clin. Immunol. (2006) 118(2) p. 403-9). These observations suggest additional benefits of P3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutical benefit for allergic indications such asthma, allergic rhinitis and atopic dermatitis.

The role of P3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of P3Kδ inhibits fMLP-dependent neutrophil chemotaxis on an ICAM coated agarose matrix integrin-dependent biased system (Sadhu et al., J. Immunol. (2003) 170(5) p. 2647-54.). Inhibition of P3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that P3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

A wide variety of retroviruses and DNA based viruses activate the PI3K pathway as a way of preventing host cell death during viral infection and ultimately exploiting the host cell synthesis machinery for its replication (Virology 344(1) p. 131-8 (2006) by Vogt et al.; and Nat. Rev. Microbiol. 6(4) p. 265-75 (2008) by Buchkovich et al.). Therefore PI3K inhibitors may have anti-viral properties in addition to more established oncolytic and anti-inflammatory indications. These antiviral effects raise interesting prospects in viral induced inflammatory exacerbations. For example, the common cold human rhinovirus (HRV) is responsible for more than 50% of respiratory tract infections but complications of these infections can be significant in certain populations. This is particularly the case in respiratory diseases such as asthma or chronic obstruction pulmonary disease (COPD). Rhinoviral infection of epithelial cells leads to a PI3K dependent cytokine and chemokine secretion (J. Biol. Chem. (2005) 280(44) p. 36952 by Newcomb et al.). This inflammatory response correlates with worsening of respiratory symptoms during infection. Therefore PI3K inhibitors may dampen an exaggerated immune response to an otherwise benign virus. The majority of HRV strains infect bronchial epithelial cells by initially binding to the ICAM-1 receptor. The HRV-ICAM-1 complex is then further internalised by endocytosis and it has been shown that this event requires PI3K activity (J. Immunol. (2008) 180(2) p. 870-880 by Lau et al.). Therefore, PI3K inhibitors may also block viral infections by inhibiting viral entry into host cells.

PI3K inhibitors may be useful in reducing other types of respiratory infections including the fungal infection aspergillosis (Mucosal Immunol. (2010) 3(2) p. 193-205 by Bonifazi et al.). In addition, PI3Kδ deficient mice are more resistant towards infections by the protozoan parasite *Leishmania major* (J. Immunol. (2009) 183(3) p. 1921-1933 by Liu et al.). Taken with effects on viral infections, these reports suggest that PI3K inhibitors may be useful for the treatment of a wide variety of infections.

PI3K inhibition has also been shown to promote regulatory T cell differentiation (Proc. Natl. Acad. Sci. USA (2008) 105(22) p. 7797-7802 by Sauer et al.) suggesting that PI3K inhibitors may serve therapeutic purposes in auto-immune or allergic indications by inducing immuno-tolerance towards self antigen or allergen. Recently the PI3Kδ isoform has also been linked to smoke induced glucocorticoid insensitivity (Am. J. Respir. Crit. Care Med. (2009) 179(7) p. 542-548 by Marwick et al.). This observation suggests that COPD patients, which otherwise respond poorly to corticosteroids, may benefit from the combination of a PI3K inhibitor with a corticosteroid.

PI3K has also been involved in other respiratory conditions such as idiopathic pulmonary fibrosis (IPF). IPF is a fibrotic disease with progressive decline of lung function and increased mortality due to respiratory failure. In IPF, circulating fibrocytes are directed to the lung via the chemokine receptor CXCR4. PI3K is required for both signalling and expression of CXCR4 (Int. J. Biochem. and Cell Biol. (2009) 41 p. 1708-1718 by Mehrad et al.). Therefore, by reducing CXCR4 expression and blocking its effector function, a PI3K inhibitor should inhibit the recruitment of fibrocytes to the lung and consequently slow down the fibrotic process underlying IPF, a disease with high unmet need.

Compounds which are PI3-kinase inhibitors may therefore be useful in the treatment of disorders associated with inappropriate kinase activity, in particular inappropriate PI3-kinase activity, for example in the treatment and prevention of disorders mediated by PI3-kinase mechanisms. Such disorders include respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain.

Attempts have been made to prepare compounds which inhibit PI3-kinase activity and a number of such compounds have been disclosed in the art.

International patent application PCT/EP2010/055666 (publication number WO2010/125082) describes compounds having the general formula (I):

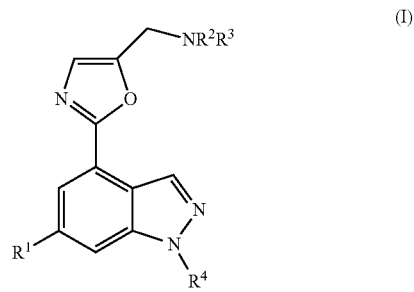

and salts thereof.

The examples of international patent application PCT/EP2010/055666 (publication number WO2010/125082) describe the preparation of N-[5-[4-(5-{[(2R,6S)-2,6-dimethyl-4-morpholinyl]methyl}-1,3-oxazol-2-yl)-1H-indazol- 6-yl]-2-(methyloxy)-3-pyridinyl]methanesulfonamide which may be represented by the formula (II):

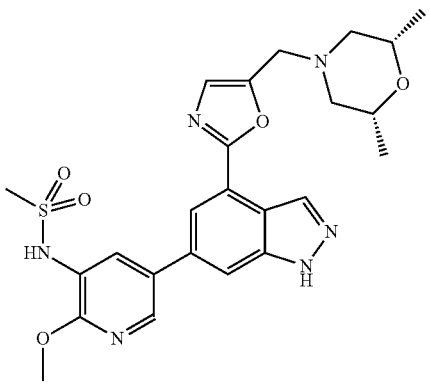

(II)

hereinafter referred to as "Compound A".

The present inventors have now found novel polymorphs and salts of Compound A.

In one embodiment, the salts of Compound A may have properties, for example solubility, which make them particularly suitable for administration as a drug, for example as an inhaled drug.

SUMMARY OF THE INVENTION

The invention is directed to novel polymorphs and salts of Compound A.

DETAILED DESCRIPTION OF THE INVENTION

In one aspect, the invention is directed to novel polymorphs of Compound A.

In one embodiment, the invention provides a polymorph (Form II) of Compound A characterised in that it provides an XRPD pattern comprising peaks (° 2θ) at about 4.6, about 9.2, about 11.4 and/or about 12.7.

In another embodiment, the invention provides a polymorph (Form II) of Compound A characterised in that it provides an XRPD pattern comprising peaks substantially as set out in Table 1.

Figure 1:
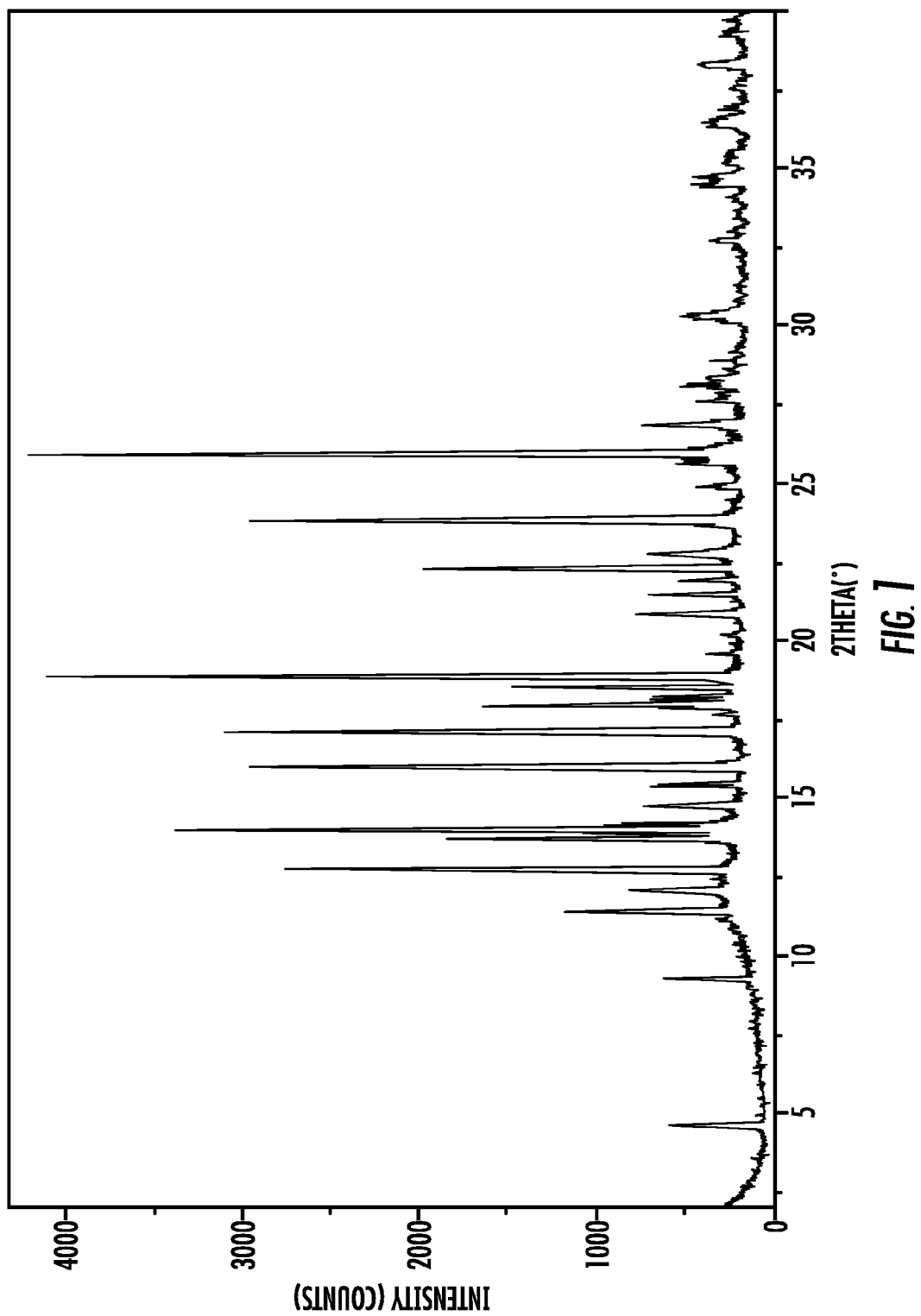
FIG. 1 shows an X-ray powder diffraction (XRPD) pattern for the Form (II) polymorph of Compound A.

In a further embodiment, the invention provides a polymorph (Form II) of Compound A characterised in that it provides an XRPD pattern substantially in accordance with FIG. 1.

In one embodiment, the invention provides a polymorph (Form III) of Compound A characterised in that it provides an XRPD pattern comprising peaks (° 2θ) at about 6.7, about 8.2, about 9.7 and/or about 12.6.

In another embodiment, the invention provides a polymorph (Form III) of Compound A characterised in that it provides an XRPD pattern comprising peaks substantially as set out in Table 2.

Figure 2:
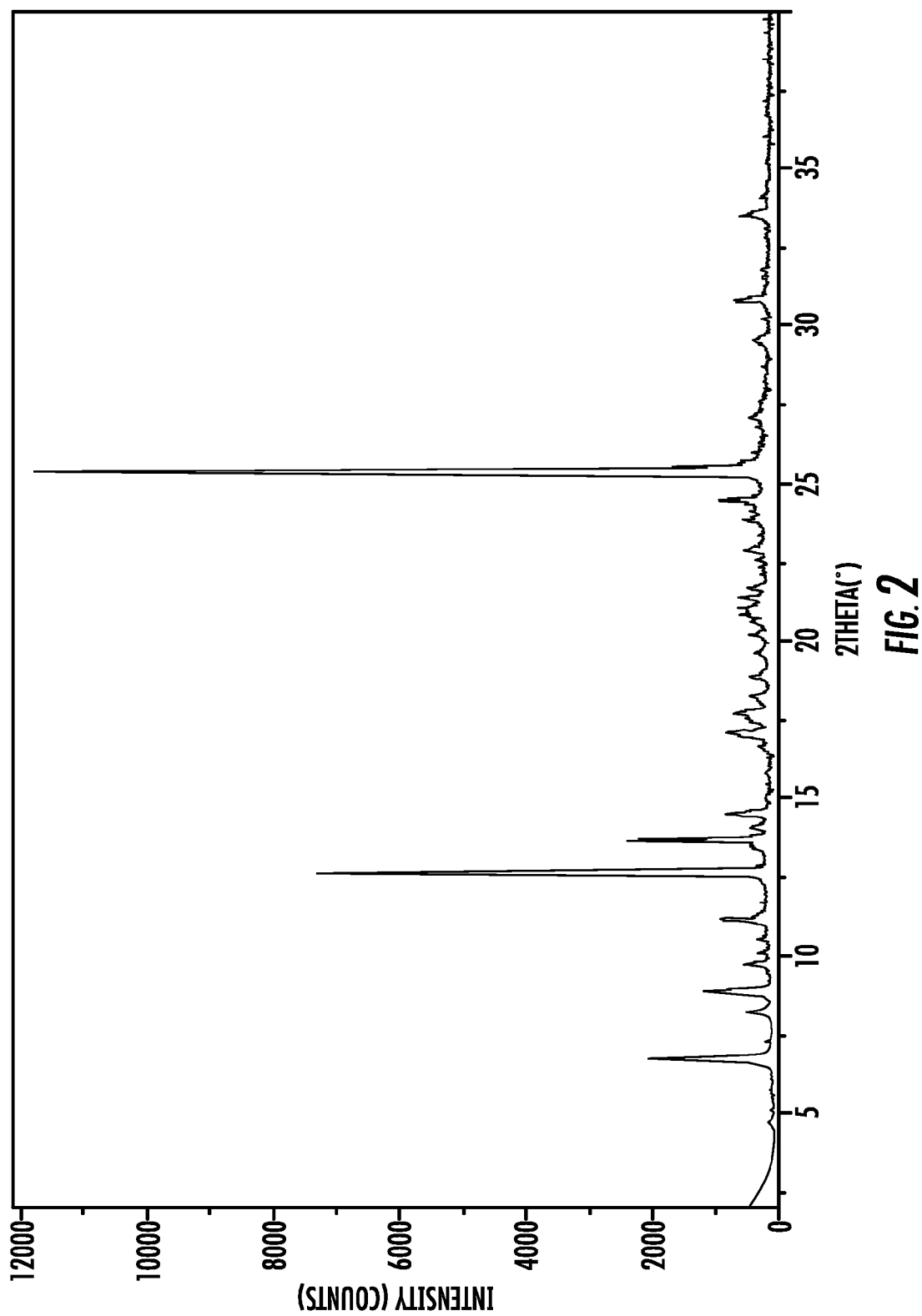
FIG. 2 shows an XRPD pattern for the Form (III) polymorph of Compound A.

In a further embodiment, the invention provides a polymorph (Form III) of Compound A characterised in that it provides an XRPD pattern substantially in accordance with FIG. 2.

In one embodiment, the invention provides a polymorph (Form IV) of Compound A characterised in that it provides an XRPD pattern comprising peaks (° 2θ) at about 5.8, and/or about 11.6.

In another embodiment, the invention provides a polymorph (Form IV) of Compound A characterised in that it provides an XRPD pattern comprising peaks substantially as set out in Table 3.

Figure 3:
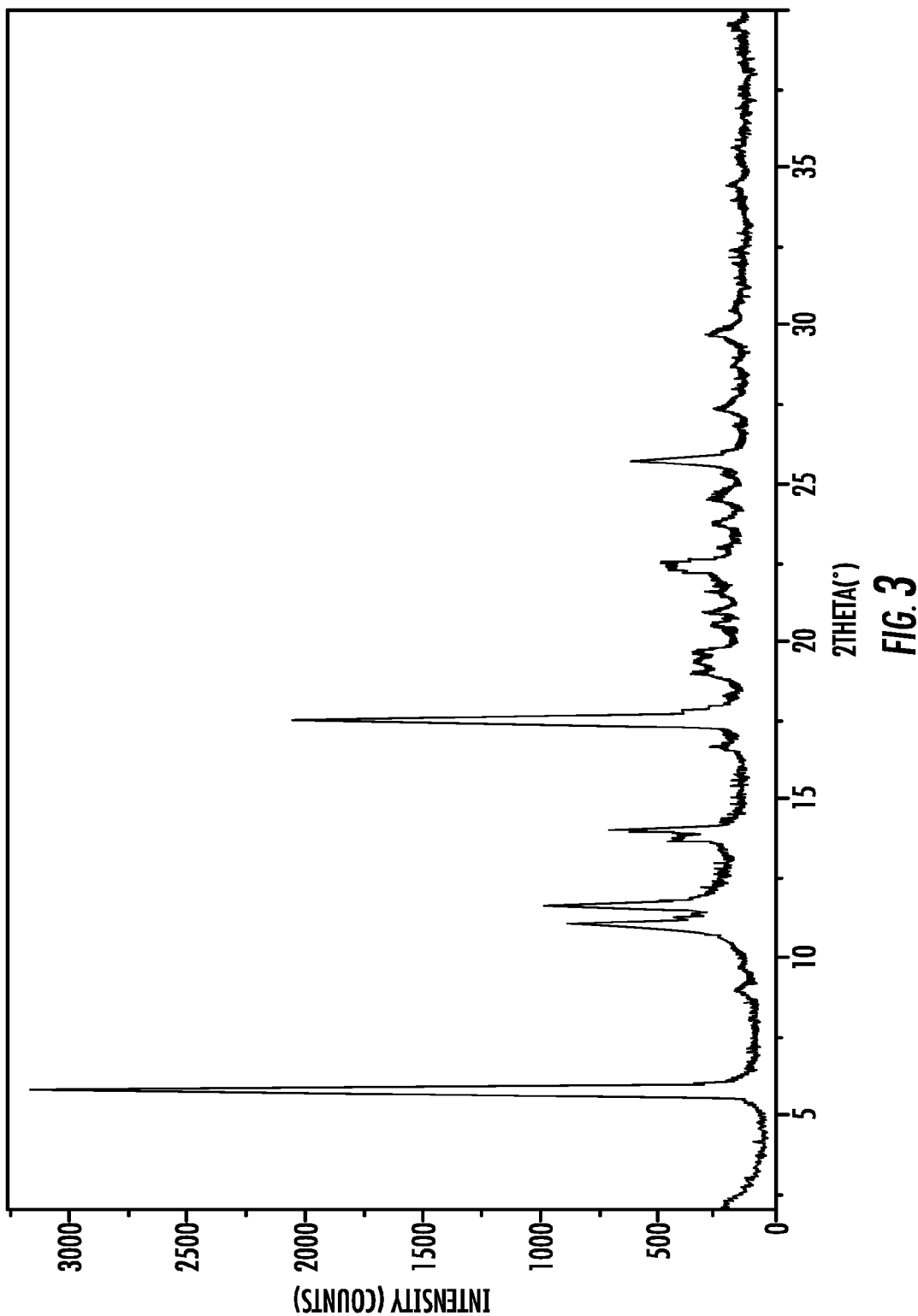
FIG. 3 shows an XRPD pattern for the Form (IV) polymorph of Compound A.

In a further embodiment, the invention provides a polymorph (Form IV) of Compound A characterised in that it provides an XRPD pattern substantially in accordance with FIG. 3.

When it is indicated herein that there is a peak in an XRPD pattern at a given value, it is typically meant that the peak is within ±0.2 of the value quoted, for example within ±0.1 of the value quoted.

In a further aspect, the invention is directed to novel salts of Compound A.

In one embodiment, the invention provides a salt of Compound A selected from sodium, tosylate, maleate, hemi pamoate, hemi naphthalenedisulfonate, mesitylenesulfonate, hemi biphenyldisulfonate, 2-naphthalenesulfonate (napsylate), hemi cinnamate, hemi sebacate, hemi pyromellitate and hemi benzenediacrylate.

In another embodiment, the invention provides a salt of Compound A selected from sodium, tosylate, maleate, hemi pamoate and hemi naphthalenedisulfonate.

In another embodiment, the invention provides a salt of Compound A selected from hemi pamoate, hemi naphthalenedisulfonate, mesitylenesulfonate, hemi biphenyldisulfonate, hemi cinnamate, hemi sebacate, hemi pyromellitate and hemi benzenediacrylate.

In another embodiment, the invention provides a salt of Compound A selected from hemi naphthalenedisulfonate, mesitylenesulfonate, hemi biphenyldisulfonate, hemi cinnamate, hemi sebacate, hemi pyromellitate and hemi benzenediacrylate.

In another embodiment, the invention provides a salt of Compound A selected from hemi pamoate and hemi naphthalenedisulfonate.

In another embodiment, the invention provides the hemi pamoate salt of Compound A.

In a further embodiment, the invention provides the hemi naphthalenedisulfonate salt of Compound A.

The sodium salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and sodium hydroxide in a stoichiometric ratio of about 1:1. The tosylate salt of Compound A is the mono tosylate salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and p-toluenesulfonic acid in a stoichiometric ratio of about 1:1. The maleate salt of Compound A is the mono maleate salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and maleic acid in a stoichiometric ratio of about 1:1. The hemi pamoate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and pamoic acid in a stoichiometric ratio of about 2:1. The hemi naphthalenedisulfonate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and naphthalenedisulfonic acid in a stoichiometric ratio of about 2:1.

The mesitylenesulfonate salt of Compound A is the mono mesitylenesulfonate salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and mesitylenesulfonic acid dihydrate in a stoichiometric ratio of about 1:1. The hemi biphenyldisulfonate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and biphenyldisulfonic acid in a stoichiometric ratio of about 2:1. The 2-naphthalenesulfonate (napsylate) salt of Compound A is the mono 2-naphthalenesulfonate (napsylate) salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and 2-naphthalenesulfonic acid in a stoichiometric ratio of about 1:1. The hemi cinnamate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and trans-cinnamic acid in a stoichiometric ratio of about 2:1. The hemi sebacate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and sebacic acid in a stoichiometric ratio of about 2:1. The hemi pyromellitate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and pyromellitic acid in a stoichiometric ratio of about 2:1. The hemi benzenediacrylate salt of Compound A is the salt formed between N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide and 1,4-benzenediacrylic acid in a stoichiometric ratio of about 2:1.

Also included within the scope of the invention are any solvates, for example hydrates, complexes and polymorphic forms of the salts of the invention.

The salts of the invention may exist in crystalline or non-crystalline form, or as a mixture thereof. For salts of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. In one embodiment, the invention provides the sodium salt of Compound A as a hydrate.

The invention encompasses the polymorphs and salts of Compound A isolated in pure form or when admixed with other materials, for example other polymorphs, or salts or solvates (inclusive of their polymorphs) of Compound A, or any other material.

Thus, in one aspect there is provided a polymorph or salt of Compound A in isolated or pure form. "Isolated" or "pure" form refers to a sample in which the polymorph or salt is present in an amount of >75%, particularly >90%, more particularly >95% and even more particularly >99% relative to other materials which may be present in the sample.

Terms And Definitions

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

CLR Controlled lab reactor
DBU 1,8-Diazabicyclo[5.4.0]undec-7-ene
DCM Dichloromethane
DMPU 1,3-Dimethyl-3,4,5,6-tetrahydro-2-(1H)-pyrimidinone
DMSO Dimethylsulfoxide
Et Ethyl
EtOAc Ethyl acetate
g Grams
h hour(s)
HPLC High performance liquid chromatography
IMS Industrial methylated spirits
IPA Isopropyl alcohol
LCMS Liquid chromatography mass spectroscopy
L Liter
M Molar
MDAP Mass directed automated preparative HPLC
Me Methyl
MeCN Acetonitrile
MeOH Methanol
mg Milligrams
mins Minutes
ml Milliliters
mmol Millimoles
Rt Retention time
RT Room temperature
SCX Strong Cation Exchange
SPE Solid Phase Extraction
TFA Trifluoroacetic acid
THF Tetrahydrofuran
UPLC Ultra high performance liquid chromatography
UV Ultraviolet All references to brine are to a saturated aqueous solution of NaCl.

Polymorph and Salt Preparation

The invention is also directed to processes for preparing the polymorphs and salts of Compound A.

In one aspect, the invention provides a process for preparing a polymorph of Compound A which comprises:
 a) stirring Compound A in a suitable solvent such as ethyl acetate or methanol, at a suitable temperature such as room temperature, or
 b) heating a saturated solution of Compound A in a suitable solvent such as tetrahydrofuran.

In a further aspect, the invention provides a process for preparing a salt of Compound A which comprises contacting Compound A with a suitable base or acid such as sodium hydroxide, p-toluenesulfonic acid, maleic acid, pamoic acid, mesitylenesulfonic acid dihydrate, biphenyldisulfonic acid, 2-naphthalenesulfonic acid, trans-cinnamic acid, sebacic acid, pyromellitic acid or 1,4-benzenediacrylic acid, in the presence or a suitable solvent such as methanol, tert-butylmethylether, tetrahydrofuran and/or isopropylacetate. In one embodiment, the invention provides a process for preparing a salt of Compound A which comprises contacting Compound A with a suitable base or acid such as sodium hydroxide, p-toluenesulfonic acid, maleic acid or pamoic acid, in the presence or a suitable solvent such as methanol, tert-butylmethylether, tetrahydrofuran and/or isopropylacetate. In a further embodiment, the invention provides a process for preparing a salt of Compound A which comprises contacting Compound A with a suitable acid such as mesitylenesulfonic acid dihydrate, biphenyldisulfonic acid, 2-naphthalenesulfonic acid, trans-cinnamic acid, sebacic acid, pyromellitic acid or 1,4-benzenediacrylic acid, in the presence or a suitable solvent such as methanol, tert-butylmethylether, tetrahydrofuran and/or isopropylacetate.

Compound A may be prepared according to known procedures, such as those disclosed in international patent application PCT/EP2010/055666 (publication number WO2010/125082) and the Examples section below. The disclosure of international patent application PCT/EP2010/055666 (publication number WO2010/125082) is incorporated herein by reference.

Methods of Use

The polymorphs and salts of the invention may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma, chronic obstructive pulmonary disease (COPD) and idiopathic pulmonary fibrosis (IPF); viral infections including viral respiratory tract infections and viral exacerbation of respiratory diseases such as asthma and COPD; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain. In one embodiment, such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain The methods of treatment of the invention comprise administering a safe and effective amount of a polymorph or salt of the invention to a patient in need thereof. Individual embodiments of the invention include methods of treating any one of the above-mentioned disorders by administering a safe and effective amount of a polymorph or salt of the invention to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a polymorph or salt of the invention or other pharmaceutically-active agent means an amount sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The polymorphs and salts of the invention may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the polymorphs and salts of the invention may be administered orally. In another embodiment, the polymorphs and salts of the invention may be administered by inhalation. In a further embodiment, the polymorphs and salts of the invention may be administered intranasally.

The polymorphs and salts of the invention may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a polymorph or salt of the invention depend on the pharmacokinetic properties of that polymorph or salt, such as absorption, distribution, and half-life, which can be determined by the skilled artisan. In addition, suitable dosing regimens, including the duration such regimens are administered, for a polymorph or salt of the invention depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

In one aspect, the invention thus provides a method of treating a disorder mediated by inappropriate PI3-kinase activity comprising administering a safe and effective amount of a polymorph or salt of the invention to a patient in need thereof.

In one embodiment, the disorder mediated by inappropriate PI3-kinase activity is selected from the group consisting of respiratory diseases (including asthma, chronic obstructive pulmonary disease (COPD) and idiopathic pulmonary fibrosis (IPF)); viral infections (including viral respiratory tract infections and viral exacerbation of respiratory diseases such as asthma and COPD); non-viral respiratory infections (including aspergillosis and leishmaniasis); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain).

In one embodiment, the disorder mediated by inappropriate PI3-kinase activity is a respiratory disease. In another embodiment, the disorder mediated by inappropriate PI3-kinase activity is asthma. In another embodiment, the disorder mediated by inappropriate PI3-kinase activity is chronic obstructive pulmonary disease (COPD). In a further embodiment, the disorder mediated by inappropriate PI3-kinase activity is idiopathic pulmonary fibrosis (IPF).

In one embodiment, the disorder mediated by inappropriate PI3-kinase activity is pain.

In one embodiment, the present invention provides a method of treating a respiratory disease comprising administering a safe and effective amount of a polymorph or salt of the invention to a patient in need thereof.

In another embodiment, the present invention provides a method of treating asthma comprising administering a safe and effective amount of a polymorph or salt of the invention to a patient in need thereof.

In one aspect, the invention provides a polymorph or salt of the invention for use in medical therapy.

In another aspect, the invention provides a polymorph or salt of the invention for use in the treatment of a disorder mediated by inappropriate PI3-kinase activity.

In a further aspect, the invention provides the use of a polymorph or salt of the invention in the manufacture of a medicament for use in the treatment of a disorder mediated by inappropriate PI3-kinase activity.

Compositions

The polymorphs and salts of the invention will normally, but not necessarily, be formulated into pharmaceutical compositions prior to administration to a patient.

Accordingly, in one aspect the invention is directed to pharmaceutical compositions comprising a polymorph or salt of the invention and one or more pharmaceutically acceptable excipients.

In another aspect the invention is directed to pharmaceutical compositions comprising 0.05 to 1000 mg of a polymorph or salt of the invention and 0.1 to 2 g of one or more pharmaceutically acceptable excipients.

In a further aspect the invention is directed to a pharmaceutical composition for the treatment or prophylaxis of a disorder mediated by inappropriate PI3-kinase activity comprising a polymorph or salt of the invention The pharmaceutical compositions of the invention may be prepared and packaged in bulk form wherein a safe and effective amount of a polymorph or salt of the invention can be extracted and then given to the patient such as with powders or syrups. Alternatively, the pharmaceutical compositions of the invention may be prepared and packaged in unit dosage form wherein each physically discrete unit contains a polymorph or salt of the invention. When prepared in unit dosage form, the pharmaceutical compositions of the invention typically may contain, for example, from 0.5 mg to 1 g, or from 1 mg to 700 mg, or from 5 mg to 100 mg of a polymorph or salt of the invention.

The pharmaceutical compositions of the invention typically contain one polymorph or salt of the invention.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the polymorph or salt of the invention when administered to a patient and interactions which would result in pharmaceutical compositions that are not pharmaceutically acceptable are avoided. In addition, each excipient must of course be pharmaceutically-acceptable eg of sufficiently high purity.

The polymorph or salt of the invention and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the polymorph or salt of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a polymorph or salt of the invention and one or more pharmaceutically acceptable excipients which comprises mixing the ingredients. A pharmaceutical composition comprising a polymorph or salt of the invention may be prepared by, for example, admixture at ambient temperature and atmospheric pressure.

In one embodiment, the polymorph or salt of the invention will be formulated for oral administration. In another embodiment, the polymorph or salt of the invention will be formulated for inhaled administration. In a further embodiment, the polymorph or salt of the invention will be formulated for intranasal administration.

In one aspect, the invention is directed to a solid oral dosage form such as a tablet or capsule comprising a safe and effective amount of a polymorph or salt of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The polymorphs and salts of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the polymorphs and salts of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a polymorph or salt of the invention. Syrups can be prepared by dissolving the a polymorph or salt of the invention in a suitably flavored aqueous solution, while elixirs are prepared through the use of a non-toxic alcoholic vehicle. Suspensions can be formulated by dispersing the polymorph or salt of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In a further embodiment, the invention is directed to a dosage form adapted for administration to a patient by inhalation via a nebulizer.

Dry powder compositions for delivery to the lung by inhalation typically comprise a polymorph or salt of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the polymorph or salt of the invention.

Aerosols may be formed by suspending or dissolving a polymorph or salt of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a polymorph or salt of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a polymorph or salt of the invention and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a polymorph or salt of the invention and a suitable powder base such as lactose or starch. Each capsule or cartridge may generally contain from 20 μg to 10 mg of the polymorph or salt of the invention. Alternatively, the polymorph or salt of the invention may be presented without excipients such as lactose.

The proportion of the active polymorph or salt in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 500 μg of a polymorph or salt of the invention. Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a polymorph or salt of the invention in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™)

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a polymorph or salt of the invention may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The polymorph or salt of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the polymorph or salt of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The polymorph and salts of the invention may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser.

Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the polymorph or salt of the invention.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the polymorph or salt of the invention may be employed with either a paraffinic or a water-miscible ointment base. Alternatively, the a polymorph or salt of the invention may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The polymorphs and salts and pharmaceutical compositions according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a polymorph or salt of the invention together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a polymorph or salt of the invention together with a $\beta_2$-adrenoreceptor agonist, and/or an anticholinergic, and/or a PDE-4 inhibitor, and/or an antihistamine.

In one embodiment, the invention encompasses a method of treating a disorder mediated by inappropriate PI3-kinase activity comprising administering a safe and effective amount of a combination comprising a polymorph or salt of the invention together with one or more therapeutically active agents.

In a further aspect, the invention provides a combination comprising a polymorph or salt of the invention which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a polymorph or salt of the invention together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of β₂-adrenoreceptor agonists include:

3-(4-{[6-({(2R)-2-hydroxy-2-[4-hydroxy-3-(hydroxymethyl)phenyl]ethyl}amino)hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl)amino]-1-hydroxyethyl}-2-(hydroxymethyl)phenol;

4-{(1R)-2-[(6-{4-[3-(cyclopentylsulfonyl)phenyl]butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The β₂-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the polymorphs or salts of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the polymorphs and salts of the invention in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393);

roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a polymorph or salt of the invention together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a polymorph or salt of the invention together with an H3 antagonist (and/or inverse agonist). Examples of H3 antagonists include, for example, those compounds disclosed in WO2004/035556 and in WO2006/045416. Other histamine receptor antagonists which may be used in combination with the polymorphs and salts of the present invention include antagonists (and/or inverse agonists) of the H4 receptor, for example, the compounds disclosed in Jablonowski et al., *J. Med. Chem.* 46:3957-3960 (2003).

The invention thus provides, in a further aspect, a combination comprising a polymorph or salt of the invention together with a PDE4 inhibitor.

The invention thus provides, in a further aspect, a combination comprising a polymorph or salt of the invention together with a $\beta_2$-adrenoreceptor agonist.

The invention thus provides, in a further aspect, a combination comprising a polymorph or salt of the invention together with a corticosteroid.

The invention thus provides, in a further aspect, a combination comprising a polymorph or salt of the invention together with a non-steroidal GR agonist.

The invention thus provides, in a further aspect, a combination comprising a polymorph or salt of the invention together with an anticholinergic.

The invention thus provides, in a further aspect, a combination comprising a polymorph or salt of the invention together with an antihistamine.

The invention thus provides, in a further aspect, a combination comprising a polymorph or salt of the invention together with a PDE4 inhibitor and a $\beta_2$-adrenoreceptor agonist.

The invention thus provides, in a further aspect, a combination comprising a polymorph or salt of the invention together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual components of such combinations may be administered either sequentially or simultaneously in separate or combined pharmaceutical formulations. In one embodiment, the individual components will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a polymorph or salt of the invention together with another therapeutically active agent.

The invention thus provides, in a further aspect, a pharmaceutical composition comprising a combination of a polymorph or salt of the invention together with a PDE4 inhibitor.

The invention thus provides, in a further aspect, a pharmaceutical composition comprising a combination of a polymorph or salt of the invention together with a $\beta_2$-adrenoreceptor agonist.

The invention thus provides, in a further aspect, a pharmaceutical composition comprising a combination of a polymorph or salt of the invention together with a corticosteroid.

The invention thus provides, in a further aspect, a pharmaceutical composition comprising a combination of a polymorph or salt of the invention together with a non-steroidal GR agonist.

The invention thus provides, in a further aspect, a pharmaceutical composition comprising a combination of a polymorph or salt of the invention together with an anticholinergic.

The invention thus provides, in a further aspect, a pharmaceutical composition comprising a combination of a polymorph or salt of the invention together with an antihistamine.

The invention thus provides, in a further aspect, a pharmaceutical composition comprising a combination of a polymorph or salt of the invention together with a PDE4 inhibitor and a $\beta_2$-adrenoreceptor agonist.

The invention thus provides, in a further aspect, a pharmaceutical composition comprising a combination of a polymorph or salt of the invention together with an anticholinergic and a PDE4 inhibitor.

The invention will now be illustrated by way of the following non-limiting examples.

EXAMPLES

The following examples illustrate the invention. These examples are not intended to limit the scope of the present invention, but rather to provide guidance to the skilled artisan to prepare and use the polymorphs, salts, compositions, and methods of the present invention. While particular embodiments of the present invention are described, the skilled artisan will appreciate that various changes and modifications can be made without departing from the spirit and scope of the invention.

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

The names of the compounds have been obtained using a compound naming programme which matches structure to name (e.g. ACD/Name Batch v 9.0).

General Experimental Details

Liquid Chromatography Mass Spectroscopy (LCMS) Methods

LCMS analysis has been carried out using one of the methods listed below.

Method A:
    LCMS instrumentation consists of the following:
    Column: Acquity UPLC BEH $C_{18}$ 1.7 µm 2.1 mm×50 mm.
Column oven set to 40 degrees centigrade
Solvent A: Water 0.1% Formic Acid+10 mM Ammonium Acetate
Solvent B: MeCN:Water 95:5+0.05% Formic Acid
Injection volume: 0.5 µl
Injection technique: Partial loop overfill
UV detection: 220 to 330 nm
UV sampling rate: 40 points per second
MS scan range: 100 to 1000 amu
MS scanning rate: 0.2 second scan with a 0.1 second inter scan delay
MS scan function: Electrospray with pos neg switching
Cycle time: 2 minutes and 30 seconds Gradient:

| Time | Flow ml/min | % A | % B |
|---|---|---|---|
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

Method B:

The HPLC analysis was conducted on a Sunfire C18 column (30 mm×4.6 mm i.d. 3.5 μm packing diameter) at 30 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.
Method C:

The HPLC analysis was conducted on a Phenomenex Luma C18(2) (50 mm×2 mm i.d. 3 μm packing diameter, or validated equivalent) at 40 degrees centigrade.
Solvent A=0.05% v/v solution of TFA in Water.
Solvent B=0.05% v/v solution of TFA in Acetonitrile.
The gradient employed was:

| Time (min) | Flow Rate (ml/min) | % A | % B |
|---|---|---|---|
| 0 | 1 | 100 | 0 |
| 8 | 1 | 5 | 95 |
| 8.01 | 1 | 100 | 0 |

The UV detection wavelength was analyte dependent and mass spectra were recorded on a mass spectrometer using positive ion electrospray.
Method D:

The HPLC analysis was conducted on a Phenomenex Luma C18(2) (50 mm×2 mm i.d. 3 μm packing diameter, or validated equivalent) at 60 degrees centigrade.
Solvent A=0.05% v/v solution of TFA in Water.
Solvent B=0.05% v/v solution of TFA in Acetonitrile.
The gradient employed was:

| Time (min) | Flow Rate (ml/min) | % A | % B |
|---|---|---|---|
| 0 | 1.5 | 100 | 0 |
| 2.5 | 1.5 | 5 | 95 |
| 2.7 | 1.5 | 5 | 95 |
| 2.9 | 1.5 | 100 | 0 |

The UV detection wavelength was analyte dependent and mass spectra were recorded on a mass spectrometer using positive ion electrospray.
Mass Directed Automated Preparative HPLC Methods The methods for the mass-directed automated preparative HPLC used for the purification of compounds are described below:
Method A—High pH Column Details: Waters_XBRIDGE Prep C18 column 5 um OBD (30×150 mm)

The solvents employed were:
A=10 mM Ammonium Bicarbonate in water adjusted to pH 10 with aq. Ammonia solution
B=Acetonitrile+0.1% aq. Ammonia Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.
Method B—Low pH Column Details: SUNFIRE C18 column (30×150 mm id 5 uM packing diameter)

The solvents employed were:
A=0.1% v/v solution of Formic Acid in Water.
B=0.1% v/v solution of Formic Acid in Acetonitrile.

Collection was triggered by uv, ms or a combination of the two. The UV detection was an averaged signal from wavelength of 210 nm to 350 nm. Mass spectra were recorded on a mass spectrometer using an alternate-scan positive and negative mode electrospray ionization.
Preparation of Compound A

INTERMEDIATES AND EXAMPLES

Intermediate 1

6-Chloro-4-iodo-1-(phenylsulfonyl)-1H-indazole

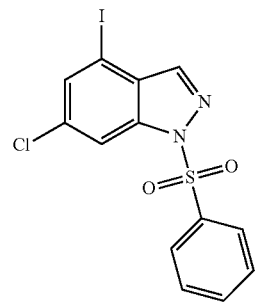 [SMILES: O=S(=O)(c1ccccc1)n1ncc2c(I)cc(Cl)cc21]

Method A

6-Chloro-4-iodo-1H-indazole (30 g, 108 mmol, available from Sinova) was dissolved in N,N-dimethylformamide (300 ml) and cooled in an ice water bath under nitrogen. Sodium hydride (5.17 g, 129 mmol) was added portionwise, maintaining the temperature below 10° C. After full addition the reaction mixture was stirred for 20 mins then benzenesulfonyl chloride (16.5 ml, 129 mmol) was added dropwise over 15 mins. The reaction was left to warm to RT overnight then poured onto ice water (2 L). The precipitated product was collected by filtration, washed with water (ca. 400 ml) and dried in a vacuum oven overnight to give the title compound (43.3 g).

LCMS (Method A): Rt 1.38 mins, MH$^+$ 419.

Method B

To a stirred solution of 6-chloro-4-iodo-1H-indazole (633.6 g) in THF (5.7 L) was added sodium hydroxide (227.4 g) followed by tetra-n-butylammonium bisulphate (38.0 g) at 20±3° C., under a nitrogen atmosphere. The mixture was stirred at 20±3° C. for 1 h 3 min, then benzenesulphonyl chloride (319 ml) was added at such a rate as to maintain the internal temperature at <25° C. Residual benzenesulphonyl chloride was rinsed into the vessel with THF (630 mL), then the mixture stirred for 1 h 10 min. The mixture was cooled to <5° C. and water (12.7 L) added at such a rate as to maintain internal temperature below 5±3° C., then the mixture stirred at 0-5° C. for 1 h 20 min. The solids were collected by vacuum filtration, washed with water (2×1.9 L), sucked dry then further dried under vacuum with a nitrogen bleed at 40° C.±3° C. overnight to give the title compound (780.8 g).

LCMS (Method C): Rt 6.28 min, MH+ 419.

Method C

All weights, volumes and equivalents are relative to 6-chloro-4-iodo-1H-indazole.

6-Chloro-4-iodo-1H-indazole (1.0 eq., 1 wt, 50 g), sodium hydroxide (2.25 eq., 0.324 wt, 16.16 g) and tetrabutylammonium hydrogensulphate (0.05 eq., 0.061 wt, 3.05 g) are stirred in THF (9.5 vols, 475 ml) at 20±3° C. under a nitrogen atmosphere for 1 hr. The mixture is cooled to 15±3° C. and benzenesulfonyl chloride (1.10 eq., 0.51 vols, 25.5 ml) was added dropwise over 20 mins maintaining the reaction temperature at <25° C. and is washed in with THF (0.5 vols, 25 ml). The resulting mixture is then stirred under a nitrogen atmosphere at 20±3° C. for at least 1 hr before checking for completion by HPLC. The reaction mixture is then added to 0.25 M hydrochloric acid solution (18 vols, 900 ml) cooled to 0±3° C. over 15 minutes maintaining the temperature of the aqueous suspension at <20° C. This is washed in with 0.25M hydrochloric acid solution (2 vols, 100 ml). The resulting orange suspension is then stirred at 2±3° C. for at least 1 hr. The solid is filtered, washed with water (2×3 vols, 2×150 ml) and sucked dry for 20 mins, then dried under high vacuum at 40° C. (±3° C.) to constant probe temperature to afford 6-chloro-4-iodo-1-(phenylsulfonyl)-1H-indazole as an orange solid.

Intermediate 2

6-Chloro-1-(phenylsulfonyl)-4-(trimethylstannanyl)-1H-indazole

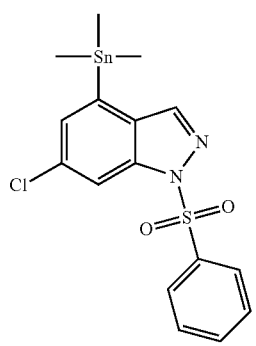 [SMILES: [CH3][Sn]([CH3])([CH3])[c]1cc(Cl)cc2c1cnn2S(=O)(=O)c1ccccc1]

6-Chloro-4-iodo-1-(phenylsulfonyl)-1H-indazole (30 g, 71.7 mmol), tetrakis(triphenylphosphine)palladium(0) (8.1 g, 7.01 mmol), xylene (200 ml), triethylamine (19.98 ml, 143 mmol) and hexamethylditin (21.8 ml, 105 mmol) were heated at 150° C. for 2 h. The reaction mixture was filtered hot through Celite, washing with further xylene and the solvent was evaporated in vacuo. The residue was triturated with cyclohexane and the precipitate collected by filtration and dried in a vacuum oven to give the title compound (14.4 g).

LCMS (Method A): Rt 1.51 mins, MH+ 457.

Intermediate 3a

Ethyl 2-[6-chloro-1-(phenylsulfonyl)-1H-indazol-4-yl]-1,3-oxazole-5-carboxylate

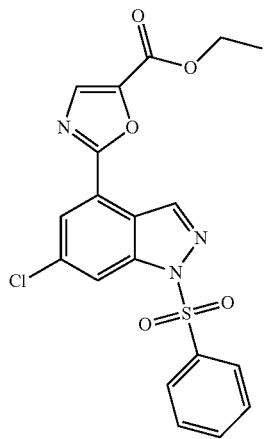 [SMILES: CCOC(=O)c1cnc(-c2cc(Cl)cc3c2cnn3S(=O)(=O)c2ccccc2)o1]

In 4 batches, tetrakis(triphenylphosphine)palladium(0) (3.37 g, 2.92 mmol), ethyl 2-chloro-1,3-oxazole-5-carboxylate (6.65 g, 37.9 mmol, available from Apollo Scientific) and copper(I) iodide (1.11 g, 5.83 mmol) were added to a solution of 6-chloro-1-(phenylsulfonyl)-4-(trimethylstannanyl)-1H-indazole (13.28 g, 29.2 mmol) in N,N-dimethylformamide (52 ml). In 3 of the batches, tetrakis(triphenylphosphine)palladium(0) (1.03 g, 0.89 mmol), ethyl 2-chloro-1,3-oxazole-5-carboxylate (2.03 g, 11.59 mmol) and copper(I) iodide (0.34 g, 1.78 mmol) were added to a solution of 6-chloro-1-(phenylsulfonyl)-4-(trimethylstannanyl)-1H-indazole (4.06 g, 8.91 mmol) in N,N-dimethylformamide (16 ml). In the fourth batch, tetrakis(triphenylphosphine)palladium(0) (0.28 g, 0.24 mmol), ethyl 2-chloro-1,3-oxazole-5-carboxylate (0.55 g, 3.14 mmol) and copper(I) iodide (0.09 g, 0.48 mmol) were added to a solution of 6-chloro-1-(phenylsulfonyl)-4-(trimethylstannanyl)-1H-indazole (1.10 g, 2.42 mmol) in N,N-dimethylformamide (4 ml). Each batch was heated and stirred at 100° C. under microwave irradiation for 30 min. The mixtures were allowed to cool to RT and the combined precipitated product suspended in diethyl ether and collected by filtration, washing with further diethyl ether then drying in a vacuum oven for 72 h. Approximately 5.2 g of the resultant solid was dissolved in dichloromethane and passed through Celite, eluting with further dichloromethane. The solvent was evaporated in vacuo to give the title compound as a pale orange solid (4.95 g).

LCMS (Method A): Rt 1.38 mins, MH+ 432.

Intermediate 3b

Methyl 2-[6-chloro-1-(phenylsulfonyl)-1H-indazol-4-yl]-1,3-oxazole-5-carboxylate

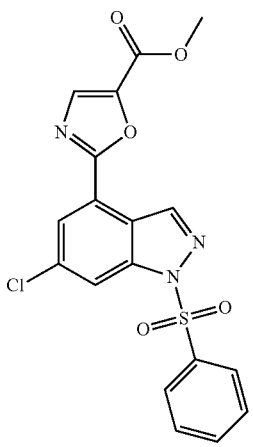 [SMILES: COC(=O)c1cnc(-c2cc(Cl)cc3c2cnn3S(=O)(=O)c2ccccc2)o1]

To a stirred solution of 6-chloro-4-iodo-1-(phenylsulphonyl)-1H-indazole (549.8 g) in toluene (1.43 L) was added triethylamine (380 ml) at 20±3° C. under an atmosphere of nitrogen. Hexamethylditin (385 ml) in toluene (825 ml) was added, followed by toluene (275 ml) then tetrakis(triphenylphosphine) palladium (0) (154.7 g). The reaction mixture was heated to 120° C. and stirred at this temperature for 3 h. The mixture was allowed to cool to 20±3° C., filtered, then washed with toluene (4.95 L). The filtrate was transferred to a clean vessel through a 5 μm Dominick hunter in-line filter, rinsing with further toluene (550 ml). The batch was then washed with 50% aqueous KF solution (5.5 L), the aqueous slurry filtered and the filtrate recombined with the organic phase. The aqueous was separated and the organics washed successively with 50% aqueous KF (5.5 L), followed by water (5.5 L). The organic layer was diluted with DMPU (2.75 L) then concentrated by vacuum distillation to ca. 5.4 vols. To the resultant solution was added copper (I) iodide (25.5 g) followed by methyl 2-chloro-1,3-oxazole-5-carboxylate (279 g, available from Apollo Scientific) at 20±3° C. The solution was degassed via vacuum and nitrogen purges (×3). Tetrakis(triphenylphosphine)palladium(0) (78 g) was added, the mixture degassed (×3) and then heated to 85-90° C. for 10 h. The mixture was diluted with DMSO (13.75 L) and cooled to 20±3° C., then water (2.75 L) added in ca. 1 vol portions over ca. 15 mins until crystallisation was initiated. The resultant suspension was aged at 20° C.±3° C. for 1.5 h. The solids were collected by vacuum filtration, washed with water (2×2.75 L), sucked dry and then further dried in vacuo with a nitrogen bleed at 45° C.±5° C. overnight to give the title compound (341.1 g).

LCMS (Method C): Rt 6.08 mins, MH$^+$ 418

Intermediate 4

{2-[6-Chloro-1-(phenylsulfonyl)-1H-indazol-4-yl]-1,3-oxazol-5-yl}methanol

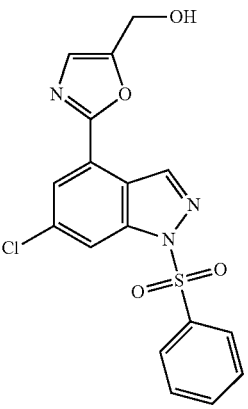 [SMILES: O=S(=O)(c1ccccc1)n1ncc2c(-c3ncc(CO)o3)cc(Cl)cc21]

Method A

A solution of ethyl 2-[6-chloro-1-(phenylsulfonyl)-1H-indazol-4-yl]-1,3-oxazole-5-carboxylate (5.11 g, 11.8 mmol) in dichloromethane (80 ml) was cooled to −25° C. in an oven dried round bottomed flask. Diisobutylaluminium hydride (25 ml, 37.5 mmol, 1.5M solution in toluene) was added dropwise and the reaction stirred at −20° C. for 3 h. A 10% aqueous solution of potassium sodium tartrate (80 ml) was added and the reaction mixture stirred for 5 min. The precipitated solid was filtered off and partitioned between ethyl acetate (500 ml) and water (500 ml). The layers were separated and the aqueous washed with further ethyl acetate (3×150 ml). The combined organics were dried and evaporated in vacuo to give the title compound as a yellow solid (1.1 g).

LCMS (Method A): Rt 1.09 mins, MH$^+$ 390.

The remaining filtrate was largely concentrated in vacuo and the residue partitioned between ethyl acetate (500 ml) and water (500 ml). The layers were separated and the aqueous extracted with further ethyl acetate (3×150 ml). The combined organics were washed with water (2×150 ml), dried over anhydrous sodium sulfate and evaporated to give the title compound as a yellow solid (1.9 g).

LCMS (Method A): Rt 1.09 mins, MH$^+$ 390.

Method B

To a solution of ethyl 2-[6-chloro-1-(phenylsulfonyl)-1H-indazol-4-yl]-1,3-oxazole-5-carboxylate (1.15 g) in THF (17.25 ml), stirred under nitrogen in an ice bath was added a solution of diisobutylaluminium hydride (5.08 ml, 5.64 mmol) in toluene. The reaction mixture was stirred at 0° C. for 2 h. Sodium sulphate decahydrate (2.5 g) was added, the mixture stirred at RT for 1 h, then filtered, washed with THF (2×5 vols) and concentrated under reduced pressure to give the title compound (0.98 g).

LCMS (Method D): Rt 2.20 mins, MH$^+$ 390.

Method C

To a solution of ethyl 2-[6-chloro-1-(phenylsulfonyl)-1H-indazol-4-yl]-1,3-oxazole-5-carboxylate (604.5 g) in THF (8.7 L), stirred under nitrogen at 0±3° C. was added a solution of approximately 1.3M diisobutylaluminium hydride (1.8 kg) in toluene. The reaction mixture was stirred at 0±3° C. for 30 mins and then diluted with THF (3 L). Sodium sulphate decahydrate (1.3 kg) was added, maintaining the temperature below 5° C. The mixture was stirred at 0±3° C. for 10 mins and was then warmed to 20±3° C. and held at this temperature for 1 h. The suspension was filtered, washed with THF (4×3 L) and concentrated under reduced pressure to give the title compound (529.6 g).

LCMS (Method C): Rt 5.18 min, MH$^+$ 390.

Method D

All weights, volumes and equivalents are relative to 6-chloro-4-iodo-1-(phenylsulfonyl)-1H-indazole.

Zinc chloride (3.6 eq, 1.17 wt, 52.7 g) in tetrahydrofuran (5 vols, 225 ml) is cooled to 0 to 5° C. A solution of the ethyl oxazole-5-carboxylate (1.1 eq, 0.37 wt, 18.1 g, corrected for 92 wt % assay) in tetrahydrofuran (5 vols, 225 ml) is added to the vessel. The suspension is cooled to −10° C. (+/−5° C.) under a nitrogen atmosphere and a 1M solution of bis-(trimethylsilyl)-lithiumamide in tetrahydrofuran (1.80 eq, 4.30 vols, 193 ml) is added over 15 minutes maintaining the temperature at −10° C. (+/−5° C.). The resulting solution is stirred under a nitrogen atmosphere at −10° C. (+/−5° C.) for 1 hour. To the solution is added 6-chloro-4-iodo-1-(phenylsulfonyl)-1H-indazole (1.0 eq, 1.0 wt, 45.0 g) and tetrakis triphenylphosphine palladium (0.03 eq, 0.083 wt, 3.73 g) (the mixture is degassed with vacuum/nitrogen 3 times) and then heated to 60° C. (+/−3° C.) for at least 6 hours. The reaction is then checked by HPLC for completion. The reaction solution is cooled to 0° C. (+/−3° C.) and a solution of 25% w/w diisobutylaluminium hydride in toluene (4.0 eq, 6.4 vols, 288 ml) is added maintaining the temperature at <5° C. The resulting reaction solution is then stirred at 0° C. (+/−3° C.) for at least 1 hour. The reaction is then checked by HPLC (generic) for completion. The reaction mixture is added portion wise to a solution of citric acid (4.0 eq, 2.0 wt, 90 g) in water (10 vols, 450 ml) at 0° C. (+/−5° C.) over ~1 h. The resulting solution is stirred at 20° C. for 15 minutes, extracted with ethyl acetate (10 vols, 450 ml), the organic layer is washed with water (2×3 vols, 2×135 ml) and filtered through a porosity 4 sinter. The organic layer is then evaporated under reduced pressure (45° C., 100 mbar) to 2 to 3 volumes, dimethyl sulphoxide (10 vols, 450 ml) is added and the solution evaporated under reduced pressure (45° C., 50 mbar) to remove all traces of other solvents. To the solution at 45° C. is added water (5 vols, 225 ml) dropwise over 30 minutes, the resulting reaction mixture is cooled to 20° C. over 3 hr and stirred at 20° C. for at least 15 hrs. The product is filtered, washed with a solution of dimethylsulphoxide:water (1:2) (2 vols, 90 ml), then washed with water (3 vols, 135 ml), then dried under high vacuum at 60° C. (±3° C.) to constant probe temperature to afford (2-(6-chloro-1-(phenylsulfonyl)-1H-indazol-4-yl)oxazol-5-yl)methanol as a beige solid.

Intermediate 5

4-[5-(Bromomethyl)-1,3-oxazol-2-yl]-6-chloro-1-(phenylsulfonyl)-1H-indazole

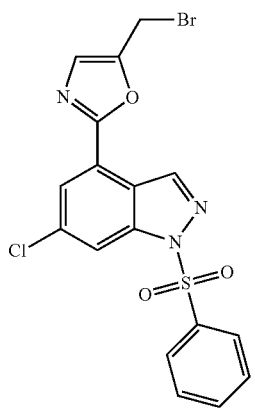 [SMILES: O=S(=O)(c1ccccc1)n1ncc2c(-c3ncc(CBr)o3)cc(Cl)cc21]

Method A

{2-[6-Chloro-1-(phenylsulfonyl)-1H-indazol-4-yl]-1,3-oxazol-5-yl}methanol (1.626 g, 4.17 mmol) was dissolved in anhydrous dichloromethane (20 ml) and carbon tetrabromide (2.77 g, 8.34 mmol) added. The reaction mixture was cooled to 0° C. and a solution of triphenylphosphine (2.188 g, 8.34 mmol) in dichloromethane (20 ml) added dropwise. After allowing to warm to RT and stirring for a further 3 h, the solvent was partially removed in vacuo and the solution purified directly by silica gel chromatography, eluting with 0-100% ethyl acetate in dichloromethane. The appropriate fractions were combined to give the title compound as a cream solid (1.16 g).

LCMS (Method B): Rt 3.70 mins, MH+ 454.

Method B

Triphenylphosphine dibromide (20.60 g, 48.8 mmol) was added to a suspension of {2-[6-chloro-1-(phenylsulfonyl)-1H-indazol-4-yl]-1,3-oxazol-5-yl}methanol (9.06 g, 23.2 mmol) in dichloromethane (181 ml) at 0° C. The reaction mixture was stirred at 0° C. until completion. Water (91 ml) and saturated sodium bicarbonate solution (91 ml) were added and the mixture stirred, then separated. The aqueous layer was extracted with further dichloromethane (45 ml) and the organics combined and washed with water (91 ml). The layers were separated and the organic concentrated to dryness then redissolved in methanol (136 ml). After stirring for 30 mins the resultant white suspension was filtered and the solid dried under vacuum to give the title compound as an off-white solid (9.58 g).

LCMS (Method D): Rt 2.57 min, MH+ 452/454.

Method C

Triphenylphosphine dibromide (1.2 kg) was added to a suspension of {2-[6-chloro-1-(phenylsulfonyl)-1H-indazol-4-yl]-1,3-oxazol-5-yl}methanol (544.7 g) in dichloromethane (3.8 L) stirred under nitrogen at 10±3° C. The reaction mixture was stirred at 10±3° C. for 20 min. Water (2.7 L) and saturated sodium bicarbonate solution (5.4 L) were added and the mixture stirred, then separated. The aqueous layer was extracted with further dichloromethane (2.7 L) and the organics combined and washed with water (2.7 L). The layers were separated and the organic concentrated to dryness then redissolved in methanol (6.5 L). After stirring for 5 hours the resultant white suspension was filtered, washed with methanol (2×1.1 L) and the solid dried under vacuum at 40±5° C. to give the title compound as an off-white solid (514.0 g).

LCMS (Method C): Rt 6.40 min, MH+ 453/455.

Method D

All weights, volumes and equivalents are relative to (2-(6-chloro-1-(phenylsulfonyl)-1H-indazol-4-yl)oxazol-5-yl)methanol.

(2-(6-Chloro-1-(phenylsulfonyl)-1H-indazol-4-yl)oxazol-5-yl)methanol (1.0 eq., 1 wt, 34.0 g) and triphenylphosphine dibromide (1.3 eq., 1.32 wt, 45.0 g) are stirred in dichloromethane (15 vols, 510 ml) at 20 (±3° C.) under a nitrogen atmosphere for 1 hr. The reaction is then checked by HPLC for completion. Once complete methanol (0.8 vols, 27.2 ml) is added to the reaction, with vigorous stirring 8% w/w sodium hydrogen carbonate solution (10 vols, 340 ml) is added drop wise over 15 minutes (check aqueous pH>7). The mixture is heated to 30° C. (±3° C.) and stirred together for 10 minutes, then separated, the aqueous is back extracted with dichloromethane (5 vols, 170 ml) and the combined dichloromethane layers are washed with water (5 vols, 170 ml). The dichloromethane solution is then evaporated under reduced pressure to a volume of approximately 4 vols. To the solution is added methanol (15 vols, 510 ml) and the solution evaporated under reduced pressure at 260 mbar, 20° C. to remove the remaining dichloromethane down to ~15 vols. The suspension is then stirred at 20° C. for at least 6 hrs. The solid is filtered, washed with methanol (2×1 vols, 2×34 ml), sucked dry for 20 minutes, then dried under high vacuum at 30° C.

(±3° C.) to constant probe temperature to afford 5-(bromomethyl)-2-(6-chloro-1-(phenylsulfonyl)-1H-indazol-4-yl)oxazole as a beige solid.

Intermediate 6

6-Chloro-4-(5-{[(2R,6S)-2,6-dimethyl-4-morpholinyl]methyl}-1,3-oxazol-2-yl)-1-(phenylsulfonyl)-1H-indazole

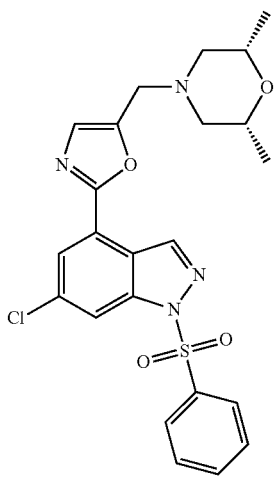 [SMILES: C[C@@H]1CN(Cc2cnc(-c3cc(Cl)cc4c3cnn4S(=O)(=O)c3ccccc3)o2)C[C@H](C)O1]

Method A

4-[5-(Bromomethyl)-1,3-oxazol-2-yl]-6-chloro-1-(phenylsulfonyl)-1H-indazole (0.580 g, 1.28 mmol) was dissolved in dichloromethane (5 ml) and (2R,6S)-2,6-dimethylmorpholine (0.317 ml, 2.56 mmol) added. The reaction mixture was stirred at RT for 3 h then the solvent removed under a stream of nitrogen. The resultant yellow solid was dissolved in dichloromethane (5 ml) and washed with water (2×2.5 ml). The layers were separated (hydrophobic frit) and the organic evaporated in vacuo to give the title compound as a pale yellow solid (0.60 g).

LCMS (Method A): Rt 0.86 mins, MH+ 487.

$^1$H NMR (400 MHz, Chloroform-d) δ (ppm) 8.93 (d, J=1.0 Hz, 1 H), 8.33 (dd, J=1.0, 1.5 Hz, 1H), 8.04-8.00 (m, 2 H), 7.98 (d, J=1.5 Hz, 1 H), 7.62 (tt, J=1.5, 7.5 Hz, 1 H), 7.51 (t, J=7.5 Hz, 2 H), 7.15 (s, 1 H), 3.67 (s, 2 H), 3.75-3.66 (m, 2 H), 2.79-2.72 (m, 2 H), 1.86 (dd, J=10.5, 11.0 Hz, 2 H), 1.16 (d, J=6.5 Hz, 6 H).

Method B (2R,6S)-2,6-dimethylmorpholine (160 ml) and then triethylamine (180 ml) were added to a suspension of 4-[5-(Bromomethyl)-1,3-oxazol-2-yl]-6-chloro-1-(phenylsulfonyl)-1H-indazole (478.1 g) in acetone (3.8 L) stirred under nitrogen at less than 25° C. The reaction mixture was stirred at 20-25° C. for 2.5 hours and then water (3.8 L) was added. The resultant suspension was stirred at than 25° C. for 35 min and was then filtered, washed with a mixture of 2:1 v/v water: acetone (2×1.0 L) and the solid dried under vacuum at 45±5° C. to give the title compound as an off-white solid (500.5 g). LCMS (Method B): Rt 3.43 min, MH+ 487.

Method C

All weights, volumes and equivalents are relative to 5-(bromomethyl)-2-(6-chloro-1-(phenylsulfonyl)-1H-indazol-4-yl)oxazole (corrected for assay).

To a suspension of 5-(bromomethyl)-2-(6-chloro-1-(phenylsulfonyl)-1H-indazol-4-yl)oxazole (1 wt, 540 g) in acetone (8.7 vol, 4.7 L) is added 2,6-dimethylmorpholine (0.33 vol, 1.2 eq, 178 ml), followed by triethylamine (0.37 vol, 1.2 eq, 200 ml) at <25° C. under a nitrogen atmosphere. The resulting mixture is stirred at 20-25° C. for at least 0.5 hr, then monitored for completion by HPLC. Water (8.7 vol, 4.7 L) is then added to the mixture over ca 5 minutes. The resulting suspension is aged at <25° C. for at least 0.5 hr, then the solids are collected by vacuum filtration, washed with water/acetone (2:1 v/v, 2×2.2 vol, 2×1.2 L) and dried in vacuo with a nitrogen bleed at 45±5° C.

Recrystallisation—All weights, volumes and equivalents are relative to ((2-(6-chloro-1-(phenylsulfonyl)-1H-indazol-4-yl)oxazol-5-yl)methyl)-cis-2,6-dimethylmorpholine. A stirred suspension of ((2-(6-chloro-1-(phenylsulfonyl)-1H-indazol-4-yl)oxazol-5-yl)methyl)-cis-2,6-dimethylmorpholine (1 wt, 30 g) in DMSO (9 vol, 270 ml) is heated to 75-80° C. under a nitrogen atmosphere. The resulting clear solution is transferred to a crystallising vessel via a 5 μm Domnick hunter in line filter, then the line is washed with further DMSO (1.0 vol, 30 ml). The hot solution is allowed to cool to 20-25° C. over at least 2 hr, then the resulting suspension is aged at this temperature for at least 1 hr. The resulting solids are filtered, washed with DMSO (1.5 vol, 45 ml), followed by water/acetone (2:1 v/v, 2×2 vol, 2×60 ml) before being sucked dry for 0.5 hr. The batch is dried in vacuo at 45° C. to constant probe temperature to afford ((2-(6-chloro-1-(phenylsulfonyl)-1H-indazol-4-yl)oxazol-5-yl)methyl)-cis-2,6-dimethylmorpholine as an off-white solid.

Intermediate 7

2-(Methyloxy)-5-(4,4,5,5-tetramethyl-1,3,2-dioxaborolan-2-yl)-3-pyridinamine

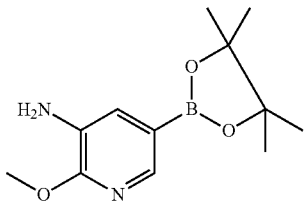

To 5-bromo-2-(methyloxy)-3-pyridinamine (18.93 g, 93 mmol, available from Asymchem International) in a 1 L round-bottom flask was added nitrogen-purged 1,4-dioxane (500 ml) followed by 4,4,4',4',5,5,5',5'-octamethyl-2,2'-bi-1,3,2-dioxaborolane (47.4 g, 186 mmol), potassium acetate (27.5 g, 280 mmol) and dichloro{1,1'-bis(diphenylphosphino)ferrocene]palladium (II) dichloromethane adduct (7.61 g, 9.32 mmol). The mixture was then stirred at 80° C. under nitrogen for 2 h. The reaction mixture was allowed to cool then partitioned between ethyl acetate and water and filtered through a Celite pad. The aqueous layer was extracted further with ethyl acetate (2×) and the combined organics washed with water, brine and dried over magnesium sulphate overnight. The mixture was filtered and the filtrate concentrated in vacuo to give a dark brown solid. The residue was purified by silica gel chromatography, eluting in 0-50% ethyl acetate/dichloromethane. The appropriate fractions were combined and evaporated to dryness and the residue triturated with cyclohexane. The resultant solid was filtered off and dried in vacuo to give the title compound as a light pink solid (11.1 g).

LCMS (Method A) Rt 0.91 mins, MH+ 251.

Intermediate 8

N-[2-(Methyloxy)-5-(4,4,5,5-tetramethyl-1,3,2-dioxaborolan-2-yl)-3-pyridinyl]methanesulfonamide

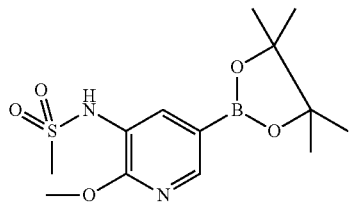 [SMILES: COc1ncc(B2OC(C)(C)C(C)(C)O2)cc1NS(C)(=O)=O]

To a solution of 2-(methyloxy)-5-(4,4,5,5-tetramethyl-1,3,2-dioxaborolan-2-yl)-3-pyridinamine (0.5 g, 1.999 mmol) in pyridine (5 ml) was added methanesulphonyl chloride (0.309 ml, 4.00 mmol) and the mixture stirred at 20° C. for 18 hr then the solvent was removed in vacuo. The residue was partitioned between saturated sodium bicarbonate solution (10 ml) and dichloromethane (20 ml), separated by hydrophobic frit and purified by silica gel chromatography, eluting with a gradient of dichloromethane and methanol to give the title compound as a brown solid (0.46 g).

LCMS (Method A): Rt 0.98 mins, MH$^+$ 329.

Intermediate 9

N-[5-[4-(5-{[(2R,6S)-2,6-Dimethyl-4-morpholinyl]methyl}-1,3-oxazol-2-yl)-1-(phenylsulfonyl)-1H-indazol-6-yl]-2-(methyloxy)-3-pyridinyl]methanesulfonamide

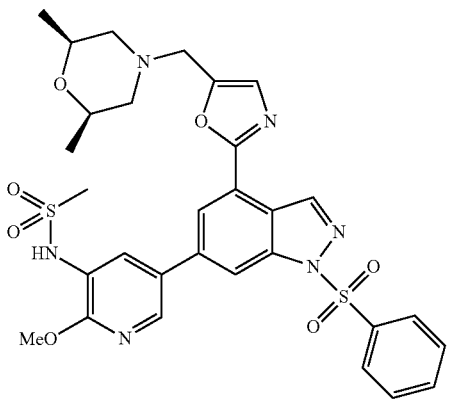 [SMILES: COc1ncc(-c2cc(-c3ncc(CN4C[C@@H](C)O[C@@H](C)C4)o3)c3cnn(S(=O)(=O)c4ccccc4)c3c2)cc1NS(C)(=O)=O]

Method A

A suspension of palladium (II) acetate (0.05 g) and tricyclohexylphosphine (0.16 g) in isopropanol (27 ml) was added to a suspension of 6-Chloro-4-(5-{[(2R,6S)-2,6-dimethyl-4-morpholinyl]methyl}-1,3-oxazol-2-yl)-1-(phenylsulfonyl)-1H-indazole (5.40 g), Potassium trifluoro{6-(methyloxy)-5-[(methylsulfonyl)amino]-3-pyridinyl}borate (6.19 g) and sodium bicarbonate (2.87 g) in isopropanol (27 ml) and water (38 ml) stirring under nitrogen at 60-65° C. The reaction mixture was stirred at 60-65° C. for 2.5 hours and was then cooled to room temperature. The resultant suspension was filtered, washed with 1:1 v/v water isopropanol (11 ml then 22 ml) and the solid dried under vacuum at 40° C. to give the title compound as a grey solid (7.73 g).

LCMS (Method B): Rt 2.59 min, MH$^+$ 653.

Method B

All weights, volumes and equivalents are relative to ((2-(6-chloro-1-(phenylsulfonyl)-1H-indazol-4-yl)oxazol-5-yl)methyl)-cis-2,6-dimethylmorpholine.

((2-(6-Chloro-1-(phenylsulfonyl)-1H-indazol-4-yl)oxazol-5-yl)methyl)-cis-2,6-dimethylmorpholine (1.00 wt, 460 g), N-(2-methoxy-5-(4,4,5,5-tetramethyl-1,3,2-dioxaborolan-2-yl)pyridin-3-yl)methanesulfonamide (0.741 wt, 1.1 eq, 341 g) and potassium phosphate (0.523 wt, 1.2 eq, 241 g) are combined in IPA (5 vol, 2.3 L) and water (5 vol, 2.3 L) in a clean CLR under nitrogen. Potassium hydrogen difluoride (0.353 wt, 2.2 eq, 163 g) is added and the mixture is heated to 75-80° C. and degassed at this temperature for at least 1 hr. In a separate vessel IPA (5 vol, 2.3 L) is degassed by being heated to reflux, then stirred for a further 20 min at this temperature under a flow of N$_2$ before being cooled to 20-25° C. under a nitrogen atmosphere. To the degassed IPA (5 vol, 2.3 L) is charged palladium (II) acetate (0.00922 wt, 0.02 eq, 4.25 g), followed by tricyclohexylphosphine (0.0230 wt, 0.04 eq, 10.6 g) and the mixture stirred at 20-25° C. for at least 0.5 hr. The resultant yellow solution is added to the reaction mixture and stirred at 75-80° C. for at least 2 hr, then monitored for completion by HPLC. The mixture is cooled to 30° C. over 1 hr and water (5 vol, 2.3 L) is added. The slurry is allowed to cool to 20° C., then aged at this temperature for at least 0.5 hr, filtered, washed with IPA:water (1:1 v/v, 2×2 vol, 2×920 ml) and sucked dry. The solid is dried in vacuo at 60° C. to constant probe temperature to afford N-(5-(4-(5-((cis-2,6-dimethylmorpholino)methyl)oxazol-2-yl)-1-(phenylsulfonyl)-1H-indazol-6-yl)-2-methoxypyridin-3-yl)methanesulfonamide as an off-white solid.

Intermediate 10

5-Bromo-2-(methyloxy)-3-nitropyridine

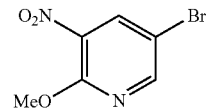

Method A

A solution of 25% wt sodium methoxide in methanol (2.1 L) was added to a suspension of 5-bromo-2-chloro-3-nitropyridine (1.70 kg) in methanol (6.6 L), stirred under nitrogen at 0-5° C. The reaction mixture was stirred at 5-10° C. for 2.75 hours and then water (8.5 L) was added. The reaction mixture was cooled to 20-25° C. The mixture was then concentrated under vacuum and the resultant suspension was filtered, washed with water (8.5 L then 2×4.25 L) and the solid dried under vacuum to give the title compound as an off-white solid (1.37 kg).

$^1$H NMR (400 MHz, Chloroform-d) δ (ppm) 8.46 (s, 1 H), 8.40 (s, 1 H).

Method B

All weights, volumes and equivalents are relative to 5-bromo-2-chloro-3-nitropyridine.

To a suspension of 5-bromo-2-chloro-3-nitropyridine (75.0 g, 1 wt, 1 eq) in methanol (300 mL, 4 vols), is added a solution of sodium methoxide in methanol (25 wt %, 88.6 g, 1.3 eq) over approximately 1 hour so as to maintain the internal temperature at 20±5° C. The mixture is stirred at 20° C. for at least 0.5 hr, then monitored for completion by HPLC. Water (375 mL, 5 vols) is then added to the mixture at such a rate as to maintain the internal temperature below 30° C., then aged at this temperature for at least 0.5 hr. The batch is then concentrated to 6 vols in vacuo. The resulting slurry is allowed to cool to 20-25° C., then collected by vacuum filtration, washed with water and dried in vacuo with a nitrogen bleed at 20-25° C. to constant weight to afford 5-bromo-2-methoxy-3-nitropyridine as a white solid.

Intermediate 11

5-Bromo-2-(methyloxy)-3-pyridinamine

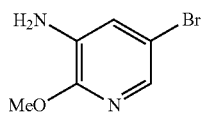

Iron powder (1.17 kg) was added to a suspension of 5-bromo-2-(methyloxy)-3-nitropyridine (1.36 kg) in IMS (6.1 L), stirred under nitrogen at 20-25° C. Water (0.8 L) was then added and the mixture cooled to less than 10° C. Aqueous hydrochloric acid (0.8 L concentrated hydrochloric acid and 0.8 L water) was then added to the reaction mixture, maintaining the temperature below 10-15° C. The suspension was warmed to 20-25° C. and then stirred at this temperature for 23 hours. The suspension was filtered, the filter cake washed with IMS (2×2.7 L) and the combined filtrates concentrated under vacuum. Water (4.1 L) was added slowly to the concentrated solution and the resulting suspension was held at 20-25° C. for 1.75 hours. The resultant suspension was filtered, washed with water (2×6.8 L) and the solid dried under vacuum to give the title compound as an off-white solid (1.13 kg).

LCMS (Method B): Rt 2.16 min, MH+ 204.

Intermediate 12

N-[5-Bromo-2-(methyloxy)-3-pyridinyl]methanesulfonamide

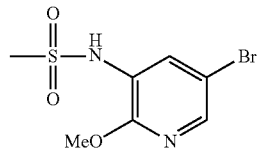

Method A

Pyridine (540 ml) was added to a suspension of 5-bromo-2-(methyloxy)-3-pyridinamine (902.0 g) in acetonitrile (2.1 L), stirred under nitrogen at less than 25° C. The mixture was cooled to less than 10° C. and methanesulfonyl chloride (605.3 g) was added maintaining the temperature below 25° C. The reaction mixture was stirred at 15-25° C. for 3 hours. Water (3.6 L) was added slowly to the mixture over 1 hour, maintaining the temperature below 25° C. The resultant suspension was filtered, washed with 3:1 v/v water:acetonitrile (2×1.35 L and the solid dried under vacuum at 45±5° C. to give the title compound as an off-white solid (1.13 kg).

LCMS (Method B): Rt 1.42 min, MH+ 282.

Method B

All weights, volumes and equivalents are relative to 5-bromo-2-methoxypyridin-3-amine hydrochloride.

5-Bromo-2-methoxypyridin-3-amine hydrochloride (100 g, 1 wt, 1 eq) is charged to a CLR containing a mixture of acetonitrile (220 mL, 2.2 vols) and pyridine (101 mL, 1.01 vols, 99 g, 0.99 wt) at room temperature. Methanesulfonyl chloride (56.4 g, 0.564 wt, 1.18 eq) is then added to the mixture over 20 minutes whilst maintaining the temperature at 20° C. Having stirred at 20° C. for a further 1.5 hours, the mixture is sampled and analysed by HPLC. The completed reaction is quenched by the addition of water over 1 hour, maintaining the mixture at 20° C. and with increased stirrer speed. The resulting slurry is stirred for 17 hours and then filtered in vacuo. The cake is washed with 3:1 water:acetonitrile (2×50 mL, 2×0.5 vols) and then dried under vacuum at 40-45° C. to afford N-(5-bromo-2-methoxypyridin-3-yl)methanesulfonamide.

Intermediate 13

Potassium trifluoro{6-(methyloxy)-5-[(methylsulfonyl)amino]-3-pyridinyl}borate

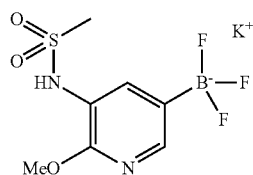 [SMILES: COc1ncc([B-](F)(F)F)cc1NS(C)(=O)=O ; [K+]]

N-[5-bromo-2-(methyloxy)-3-pyridinyl]methanesulfonamide (499.4 g), bis(pinacolato)diboron (498.2 g) and potassium acetate (361.8 g) were charged to the reaction vessel. The reaction vessel was purged with nitrogen for 10 min before 1,4-dioxane (8.0 L) was added. The resultant solution was heated to 95±5° C. and stirred under nitrogen at this temperature. A degassed solution of tris(dibenzylidene acetone)dipalladium (0) (16.6 g) and tricyclohexylphosphine (25.0 g) in 1,4-dioxane (2.5 L) was added to the reaction vessel over 30 min. The reaction mixture was then stirred at 95±5° C. for 14 hours. The mixture was cooled to 20±3° C. and held at this temperature for 1 hour. The reaction mixture was filtered and concentrated under vacuum. Water (1.0 L) and potassium hydrogenfluoride (555.0 g) were added and the resultant mixture was stirred for 1 hour. Water (2.0 L) was added to the suspension, the aqueous layer was removed and the remaining organic layer was filtered. 1,4-dioxane (12.0 L) was added to the solution which was then dried by azeotropic vacuum distillation. Upon complete distillation the mixture was cooled to 20±3° C. and held at this temperature for 30 min. The resultant suspension was filtered, washed with 1,4-dioxane (2×1 L), then t-butyl methyl ether (2×1.0 L) and the solid dried under vacuum to give the title compound as an off-white solid (708.3 g).

LCMS (Method C): Rt 2.26 min, MH+ 247.

Intermediate 14

Ethyl oxazole-5-carboxylate

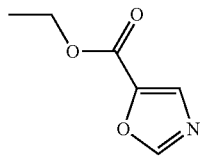

All weights, volumes and equivalents are relative to toluenesulfonylmethyl isocyanide.

Toluenesulfonylmethyl isocyanide (TosMIc) (12.31 g, 1 wt, 1 eq) is dissolved in DCM (61.6 ml, 5 vols) at 0° C. under $N_2$. In a seperate vessel, ethyl glyoxalate (50 wt % solution in toluene, 20.6 g, 20.0 ml, 1.67 wt) is diluted with DCM (61.6 ml, 5 vols) under $N_2$ and DBU (12.48 g, 12.35 ml, 1.3 eq, 1.01 wt) is added resulting in a purple solution. The second solution is added to the TosMIc solution over 1 hr, maintaining temperature at 0° C., then checked by HPLC for completion after a further 20 mins. The reaction is quenched by slow addition of 2M HCl (10 vols, 123 ml) and the DCM layer separated. The aqueous layer is re-extracted with DCM (5 vols, 61.6 ml), and the combined organics dried over $Na_2SO_4$, then evaporated on Buchi, 25° C., 100 mbar to remove DCM and toluene. Distilled at 12 mbar, jacket temperature 105° C., vapour temperature 60-80° C. to afford ethyl oxazole-5-carboxylate as a colourless oil.

Intermediate 15

5-Bromo-2-methoxypyridin-3-amine

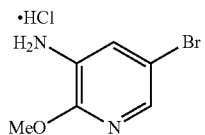

All weights, volumes and equivalents are relative to 5-bromo-2-methoxy-3-nitropyridine.

To a nitrogen-purged flask is charged 5-bromo-2-methoxy-3-nitropyridine (1 wt, 5.0 g) and iron powder (325 mesh, 0.86 wt, 4.31 g). IMS (12 vols, 60 ml) is added water (0.6 vols, 3 ml) and the mixture is heated to 35-40° C. with vigorous stirring. A mixture of concentrated HCl (37 wt %, 0.146 vols, 0.73 ml) and water (0.56 vols, 2.8 ml) is prepared. The acid solution is added to the reaction over at least 2.5 hrs at 35-40° C. The reaction is stirred for at least a further 1.5 hrs and sampled for completion test by HPLC. The reaction is cooled, filtered through Celite and the vessel and bed washed with IMS (2×2 vols, 2×10 ml). The combined filtrates are distilled under vacuum to 5 vols and toluene (10 vols, 50 ml) is added, the mixture is distilled, this is repeated until the level of IMS is <5% by NMR. The solution is cooled and 5M HCl in IPA (0.9 vols, 1.05 eq, 4.5 ml), is added over at least 30 mins. The resultant slurry is stirred for at least 60 mins, filtered and the cake washed with toluene (2×2 vols, 2×10 ml). The cake is dried under vacuum at 40° C. overnight to afford 5-bromo-2-methoxypyridin-3-amine hydrochloride as a white solid.

Intermediate 16

N-(2-Methoxy-5-(4,4,5,5-tetramethyl-1,3,2-dioxaborolan-2-yl)pyridin-3-yl)methanesulfonamide

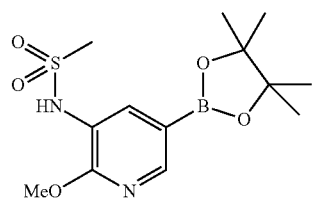 [SMILES: COc1ncc(B2OC(C)(C)C(C)(C)O2)cc1NS(C)(=O)=O]

All weights, volumes and equivalents are relative to N-(5-bromo-2-methoxypyridin-3-yl)methanesulfonamide.

Tricyclohexylphosphine (0.1191 g, 0.425 mmol, 0.008 eq, 0.008 wt) and $Pd_2(dba)_3$ (0.1438 g, 0.157 mmol, 0.003 eq, 0.01 wt) are mixed together and then toluene (15.00 mL, 1 vol, 0.86 wt, sparged with nitrogen for 1 hr) is added. The mixture is stirred and heated to 40-45° C. for 45 mins before being allowed to cool back to room temp and sit under nitrogen to give an orange-gold solution with suspended black particulates. In a separate vessel, N-(5-bromo-2-methoxypyridin-3-yl)methanesulfonamide (15.0323 g, 53.5 mmol, 1 wt, 1 eq), bis(pinacolato)diboron (16.2962 g, 64.2 mmol, 1.2 eq, 1.08 wt) and potassium acetate (10.4879 g, 107 mmol, 2 eq, 0.70 wt) are mixed together with toluene (150 mL, 10 vols, 8.6 wt). The resultant slurry is stirred and heated to 90° C. under a flow of nitrogen. Having reached the desired temperature, the catalyst mixture is added over 10 minutes followed by a wash of toluene (7.50 mL, 0.5 vol, 0.43 wt). The mixture is stirred at 90° C. for at least one hour and then sampled for HPLC analysis. Once complete, the reaction mixture is cooled to 50° C. and filtered to remove inorganic material. The filtered solid is washed with toluene (2×15 mL, 2×1 vol, 2×0.86 wt) and the liquors and washes combined and distilled down to 5 vols. The product solution is allowed to cool to room temperature by which stage it has become a slurry. Heptane (75 mL, 5 vols, 3.4 wt) is slowly added to the slurry. The slurry is aged and the supernatant analysed by HPLC to ensure sufficient crystallisation has occurred. The slurry is filtered and the solid product is washed with 1:1 toluene: heptane (2×15 mL, 2×1 vol) and dried under vacuum at 40-50° C. to afford N-(2-methoxy-5-(4,4,5,5-tetramethyl-1,3,2-dioxaborolan-2-yl)pyridin-3-yl)methanesulfonamide as an off-white solid.

Recrystallisation—All weights, volumes and equivalents are relative to N-(2-methoxy-5-(4,4,5,5-tetramethyl-1,3,2-dioxaborolan-2-yl)pyridin-3-yl)methanesulfonamide. A stirred suspension of N-(2-methoxy-5-(4,4,5,5-tetramethyl-1,3,2-dioxaborolan-2-yl)pyridin-3-yl)methanesulfonamide (1 wt, 1.01 kg) in propan-2-ol (4 vol, 4.05 L) is heated to 70-75° C. under a nitrogen atmosphere, then aged at this temperature for at least 2 hr. The batch is allowed to cool to 20-25° C. over at least 1 hr, then the suspension is aged at this temperature for a further 1 hr. The liquors are sampled by HPLC to ensure complete crystallisation, then the resulting solids are filtered, washed with propan-2-ol (2×1 vol, 2×1.01 L) before being sucked dry for 0.5 hr, then the batch is dried in vacuo at 50° C. to constant probe temperature to afford N-(2-methoxy-5-(4,4,5,5-tetramethyl-1,3,2-dioxaborolan-2-yl)pyridin-3-yl)methanesulfonamide as a white solid.

Example 1

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide

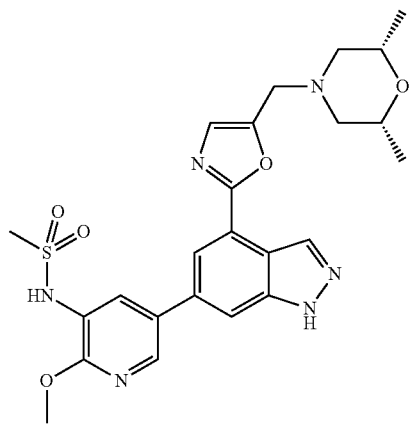

Method A

To a solution of 6-chloro-4-(5-{[(2R,6S)-2,6-dimethyl-4-morpholinyl]methyl}-1,3-oxazol-2-yl)-1-(phenylsulfonyl)-1H-indazole (0.20 g, 0.411 mmol) and N-[2-(methoxy)-5-(4,4,5,5-tetramethyl-1,3,2-dioxaborolan-2-yl)-3-pyridyl]methanesulfonamide (0.175 g, 0.534 mmol) in 1,4-dioxane (2 ml) was added chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.5 mg, 0.021 mmol), potassium phosphate tribasic (0.262 g, 1.23 mmol) and water (0.2 ml). The reaction mixture was heated and stirred at 120° C. under microwave irradiation for 1 h. Additional chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (11.5 mg, 0.021 mmol) and potassium phosphate tribasic (80 mg) were added and the reaction heated to 120° C. under microwave irradiation for 1 h. Additional potassium phospate tribasic (80 mg) was added and the reaction heated under the same conditions for a further 1 h. The reaction mixture was filtered through a silica SPE and eluted with methanol. The solvent was removed in vacuo and the residue partitioned between dichloromethane (5 ml) and water (5 ml). The layers were separated and the aqueous extracted with further dichloromethane (2×2 ml). The combined organics were concentrated under a stream of nitrogen and the residue dissolved in MeOH:DMSO (3 ml, 1:1, v/v) and purified by MDAP (method A) in 3 injections. The appropriate fractions were combined and concentrated to give a white solid which was dissolved in MeOH:DMSO (1 ml, 1:1, v/v) and further purified by MDAP (method B). The appropriate fractions were basified to pH 6 with saturated sodium bicarbonate solution and extracted with ethyl acetate (2×25 ml). The combined organics were dried and evaporated in vacuo to give a white solid which was further dried under nitrogen at 40° C. for 3 h to give the title compound as a white solid (26 mg).

LCMS (Method A): Rt 0.53 mins, MH$^+$ 513.

Method B

N-[2-(Methyloxy)-5-(4,4,5,5-tetramethyl-1,3,2-dioxaborolan-2-yl)-3-pyridinyl]methanesulfonamide (101 g, 308 mmol), 6-chloro-4-(5-{[(2R,6S)-2,6-dimethyl-4-morpholinyl]methyl}-1,3-oxazol-2-yl)-1-(phenylsulfonyl)-1H-indazole (83.3 g, 154 mmol) and sodium bicarbonate (38.8 g, 462 mmol) were suspended in 1,4-dioxane (1840 ml) and water (460 ml) under nitrogen and heated to 80° C. Chloro[2'-(dimethylamino)-2-biphenylyl]palladium-1(1R,4S)-bicyclo[2.2.1]hept-2-yl[(1S,4R)-bicyclo[2.2.1]hept-2-yl]phosphane (8.63 g, 15.40 mmol) was added and the mixture stirred overnight at 80° C.

The reaction mixture was cooled to 45° C., sodium hydroxide 2M aq. (770 ml, 1540 mmol) added and the reaction heated to 45° C. for 4 hours. The mixture was cooled to RT and diluted with water (610 mL). Dichloromethane (920 mL) was added, and the mixture was filtered twice through Celite (washed with 200 mL 1,4-dioxane/DCM 2:1 each time). The phases were separated, and aqueous washed with 1,4-dioxane/DCM 2:1 (500 mL). The aqueous phase was neutralised with hydrochloric acid to pH ~7 and extracted with 1,4-dioxane/DCM 2:1 (1 L), then 1,4 dioxane/DCM 1:1 (2×500 mL). The organics were washed with brine (500 mL), and filtered through Celite (washed with 200 mL 1,4 dioxane/DCM 2:1), and evaporated to yield a dark black solid, which was purified in 4 batches:

Batch 1: 28 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (14.78 g).

Batch 2: 30 g was dissolved in methanol and mixed with Fluorisil. The solvent was then removed by evaporation and the solid purified by column chromatography (1.5 kg silica column, solid sample injection module), eluting with Toluene/Ethanol/Ammonia 80:20:2 to give the title compound as an off-white solid (9.44 g).

Batch 3: 31 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (17 g).

Batch 4: 29 g was dissolved in Toluene/Ethanol/Ammonia 80:20:2 (100 mL) and purified by column chromatography (1.5 kg silica column), eluting with Toluene/Ethanol/Ammonia 80:20:2 to give the title compound as an off-white solid (21 g).

The mixed fractions from the 4 columns were combined and evaporated to yield 19 g which was dissolved in 200 mL of Toluene/Ethanol/Ammonia 80:20:2 (+additional 4 ml of 0.88 NH3 to help solubility) then purified by column chromatography (1.5 kg silica column), eluting with Toluene/Ethanol/Ammonia 80:20:2 to give the title compound as an off-white solid (6.1 g).

All pure batches were combined (68 g) and recrystallised from ethanol (1200 mL). The suspension was heated to reflux and a solution formed. The resulting solution was then cooled to room temperature overnight. The resulting solid was then collected by filtration, washed sparingly with ethanol and dried under vacuum to give the title compound as an off-white solid (56 g). This material was recrystallised again from ethanol (1100 mL). The suspension was heated to reflux and a solution formed. The resulting solution was then cooled to room temperature overnight with stirring. The resulting solid was collected by filtration and washed sparingly with ethanol. The solid was dried in vacuo at 60° C. for 5 hrs to give the title compound as an off-white solid (45.51 g).

LCMS (Method A): Rt 0.61 mins, MH$^+$ 513.

The filtrate from the two recrystallisations was evaporated to yield ~23 g of a solid residue that was dissolved in 200 mL of Toluene/Ethanol/Ammonia 80:20:2 (+additional 4 ml of 0.88 NH3 to help solubility) then purified by column chromatography (1.5 kg silica column), eluting with Toluene/Ethanol/Ammonia 80:20:2 to give a further crop of the title compound as an off-white solid (18.5 g). This solid was then recrystallised from ethanol (370 mL). The suspension was heated to reflux then the resulting solution stirred for 20 mins before being allowed to cool to room temperature naturally overnight. The solid was then dried in vacuo at 65° C. overnight to give the title compound as an off-white solid (11.90 g).

LCMS (Method A): Rt 0.62 mins, MH+ 513.

Method C

10M Sodium hydroxide solution (0.70 ml) was added to a stirred suspension of N-[5-[4-(5-{[(2R,6S)-2,6-dimethyl-4-morpholinyl]methyl}-1,3-oxazol-2-yl)-1-(phenylsulfonyl)-1H-indazol-6-yl]-2-(methyloxy)-3-pyridinyl]methanesulfonamide (1.17 g) in water (5.8 ml). The resulting mixture was stirred at room temperature for 3.75 hours and was then washed with ethyl acetate (2×6 ml). The layers were separated and the aqueous phase was acidified to pH 6 with 2M hydrochloric acid (0.8 ml). The acidified aqueous layer was extracted twice with ethyl acetate (11 ml then 5 ml). The combined ethyl acetate extracts were dried by azeotropic distillation and diluted with further ethyl acetate (11 ml). The misture was stirred at room temperature for 112 hours. The slurry was seeded and then stirred at room temperature for 48 hours. The resultant suspension was filtered, washed with ethyl acetate (2×2 ml) and the solid dried under vacuum at 40° C. to give the title compound as a pale yellow solid (0.58 g).

LCMS (Method B): Rt 1.86 min, MH+ 513.

Method D

To a suspension of N-[5-[4-(5-{[(2R,6S)-2,6-dimethyl-4-morpholinyl]methyl}-1,3-oxazol-2-yl)-1-(phenylsulfonyl)-1H-indazol-6-yl]-2-(methyloxy)-3-pyridinyl]methanesulfonamide (596.5 g, 0.91 mol) in water (3.8 L) is added 5M sodium hydroxide (715 ml, 3.56 mol) over 20 mins at <25° C. The mixture is stirred at 20±3° C. for 2 h 45 min then washed with EtCN (3 L). The pH of the basic aqueous phase is adjusted to pH 6.6 using 2M hydrochloric acid (1.4 L), maintaining the temperature below 30° C. The mixture is then extracted with MeTHF (2×4.8 L), and the combined MeTHF extracts are washed with water (1.2 L). The mixture is concentrated to approx 2.4 L and EtOAc (3 L) is added. This put and take distillation is repeated a further 3 times. The mixture is adjusted to 60±3° C. and seeded twice (2×3 g) 35 mins apart. The resultant is aged for 1 h 10 mins then cooled over 2 h to 20-25° C., and aged for a further 15 h 50 min. The slurry is filtered, washed with EtOAc (2×1.2 L) and dried in vacuo at 45±5° C. for approx 3 day to give the title compound.

Preparation of Polymorphs of Compound A

Form (II)

Ethyl acetate (15 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (2.1 g) and was stirred at ambient conditions overnight. The resultant slurry was filtered and dried under vacuum at 50° C. to give a new solid state form (91 ckw/w).

1H NMR (400 MHz, DMSO d6) d=13.49 (br s, 1H), 9.39 (s, 1H), 8.58 (s, 1H), 8.42 (d, J=2.2 Hz, 1H), 7.99 (d, J=2.2 Hz, 1H), 7.93 (d, J=1.2 Hz, 1H), 7.88 (s, 1H), 7.35 (s, 1H), 4.00 (s, 3H), 3.74 (s, 2H), 3.58 (m, 2H), 3.11 (s, 3H), 2.80 (d, J=10.3 Hz, 2H), 1.78 (t, J=10.3 Hz, 2H), 1.05 (d, J=6.4 Hz, 6H)

Form (III)

Methanol (4 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) followed by fumaric acid (0.0764 g) in methanol (2 ml). The resultant suspension was diluted further with methanol (3 ml) and stirred overnight at ambient conditions. The suspension was filtered, washed with methanol and air dried to give a new solid state form (64% w/w).

1H NMR (400 MHz, DMSO d6) d=13.50 (br s, 1H), 9.39 (s, 1H), 8.58 (s, 1H), 8.42 (d, J=2.2 Hz, 1H), 7.99 (d, J=2.2 Hz, 1H), 7.93 (d, J=1.2 Hz, 1H), 7.88 (s, 1H), 7.35 (s, 1H), 4.00 (s, 3H), 3.74 (s, 2H), 3.58 (m, 2H), 3.11 (s, 3H), 2.80 (d, J=10.3 Hz, 2H), 1.78 (t, J=10.5 Hz, 2H), 1.05 (d, J=6.4 Hz, 6H)

Form (IV)

Tetrahydrofuran was saturated with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide at room temperature and heated. The suspension was cooled to room temperature and solids filtered, washed with THF and dried under vacuum at 30° C. to give a new solid state form.

1H NMR (400 MHz, DMSO d6) d=13.50 (br s, 1H), 9.39 (s, 1H), 8.58 (s, 1H), 8.41 (d, J=2.0 Hz, 1H), 7.98 (d, J=2.2 Hz, 1H), 7.93 (d, J=0.7 Hz, 1H), 7.88 (s, 1H), 7.35 (s, 1H), 4.00 (s, 3H), 3.74 (s, 2H), 3.58 (m, 2.4H), 3.11 (s, 3H), 2.80 (d, J=10.5 Hz, 2H), 1.78 (t, J=10.5 Hz, 2.4H), 1.05 (d, J=6.1 Hz, 6H)

Sample contains 0.2 molar equivalents tetrahydrofuran

X-Ray Powder Diffraction (XRPD) for Forms (II) to (IV)

The data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

Form (III) was lightly ground with pestle and mortar to reduce preferred orientation.

Form (II)

The XRPD data are shown in FIG. 1.

Characteristic XRPD angles and d-spacings for the solid state form are summarised in Table 1. Peak positions were measured using Highscore software.

TABLE 1

| 2θ/° | d-spacing/Å |
| --- | --- |
| 4.6 | 19.1 |
| 9.2 | 9.6 |
| 11.4 | 7.8 |
| 12.1 | 7.3 |
| 12.7 | 7.0 |
| 13.7 | 6.5 |
| 14.0 | 6.3 |
| 16.0 | 5.5 |
| 17.1 | 5.2 |
| 17.9 | 5.0 |
| 18.5 | 4.8 |
| 18.8 | 4.7 |
| 22.3 | 4.0 |
| 20.8 | 4.3 |
| 23.8 | 3.7 |
| 25.9 | 3.4 |

Form (III)

The XRPD data are shown in FIG. 2.

Characteristic XRPD angles and d-spacings for the solid state form are summarised in Table 2. Peak positions were measured using Highscore software.

TABLE 2

| 2θ/° | d-spacing/Å |
|---|---|
| 6.7 | 13.2 |
| 8.2 | 10.8 |
| 8.8 | 10.0 |
| 9.7 | 9.1 |
| 11.1 | 8.0 |
| 12.6 | 7.0 |
| 13.6 | 6.5 |
| 14.4 | 6.1 |
| 17.0 | 5.2 |
| 17.7 | 5.0 |
| 18.8 | 4.7 |
| 20.9 | 4.2 |
| 21.3 | 4.2 |
| 22.8 | 3.9 |
| 24.4 | 3.6 |
| 25.3 | 3.5 |

Form (IV)

The XRPD data are shown in FIG. 3.

Characteristic XRPD angles and d-spacings for the solid state form are summarised in Table 3. Peak positions were measured using Highscore software.

TABLE 3

| 2θ/° | d-spacing/Å |
|---|---|
| 5.8 | 15.2 |
| 11.1 | 8.0 |
| 11.6 | 7.6 |
| 14.0 | 6.3 |
| 17.5 | 5.1 |
| 19.3 | 4.6 |
| 22.3 | 4.0 |
| 25.7 | 3.5 |

Preparation of Salts of Compound A

Sodium Salt

Methanol (2 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) followed by aqueous sodium hydroxide (0.129 ml) to give a solution. Tert-butylmethylether (4 ml) was added to the solution followed by seed crystals of the sodium salt and this suspension was stirred overnight at ambient conditions. The suspension was filtered, washed with tert-butylmethylether (2 ml) and air dried to give the sodium salt (0.2312 g) as a hydrate.

NMR: Consistent with salt formation $^1$H NMR (400 MHz, DMSO d6) d=13.35 (br s, 1H), 8.53 (s, 1H), 7.90 (d, J=1.2 Hz, 1H), 7.73 (s, 1H), 7.65 (d, J=2.5 Hz, 1H), 7.62 (d, J=2.2 Hz, 1H), 7.33 (s, 1H), 4.00 (s, 3H), 3.80 (s, 3H), 3.59 (m, 2H), 2.83 (d, J=10.3, 2H), 2.61 (s, 3H), 1.78 (t, J=10.5 Hz, 2H), 1.05 (d, J=6.1 Hz, 6H)

Tosylate Salt

A solution of N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) in tetrahydrofuran (3 ml) was added to p-toluenesulfonic acid (0.1224 g) to give initially a solution. A suspension formed on stirring and was diluted with tetrahydrofuran (2 ml) and stirred overnight at ambient conditions. The suspension was filtered, washed with tetrahydrofuran (2 ml) and air dried to give the tosylate (0.3759 g).

NMR: Consistent with mono tosylate formation $^1$H NMR (400 MHz, DMSO d6) d=13.56 (br s, 1H), 10.38 (br s, 1H), 9.43 (s, 1H), 8.69 (s, 1H), 8.43 (d, J=2.5 Hz, 1H), 8.03 (s, 1H), 7.99 (d, J=2.2 Hz, 1H), 7.96 (s, 1H), 7.69 (s, 1H), 7.46 (d, J=7.8 Hz, 2H), 7.11 (d, J=7.8 Hz, 2H), 4.69 (br s, 2H), 4.00 (s, 3H), 3.80 (br s, 2H), 3.50 (br s, 2H), 3.11 (s, 3H), 2.80 (br s, 2H), 2.28 (s, 3H), 1.05 (d, J=6.1 Hz, 6H) Sample contains 0.5 molar equivalents tetrahydrofuran NMR signals 3.60 (m, 2H), 1.76 (m, 2H)

Maleate Salt

Methanol (4 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.3 g) followed by maleic acid (0.0749 g) in methanol (2 ml). The solution was allowed to crystallise overnight at ambient conditions. The resultant suspension was filtered, washed with methanol (1 ml) and air dried to give the maleate (0.1441 g).

NMR: Consistent with mono maleate formation $^1$H NMR (400 MHz, DMSO d6) d=13.53 (br s, 1H), 9.41 (s, 1H), 8.63 (s, 1H), 8.42 (d, J=2.4 Hz, 1H), 7.99 (d, J=2.4 Hz, 1H), 7.98 (d, J=1.2 Hz, 1H), 7.92 (s, 1H), 7.51 (s, 1H), 6.16 (s, 2H), 4.16 (br s, 2H), 4.00 (s, 3H), 3.69 (br s, 2H)*, 3.11 (s+br s, 3H+2H), 2.22 (br s, 2H), 1.10 (d, J=6.4 Hz, 6H)

*Partial increase in integral due to overlap with broad HOD peak

Hemi Pamoate Salt

Tetrahydrofuran (1 ml) was added to pamoic acid (0.0759 g) to give a suspension. This suspension was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.2 g). Further tetrahydrofuran (7 ml) and water (12 ml) were added before the solution was reduced in volume by ca. 10% under a nitrogen flow. The resultant suspension was sonicated and stirred at ambient conditions overnight. The suspension was filtered, washed with water and dried under vacuum at 50° C. to give the hemi pamoate (0.092 g) containing 5% w/w water.

NMR: Consistent with hemi pamoate formation $^1$H NMR (400 MHz, DMSO d6) d=13.51 (br s, 1H), 9.40 (s, 1H), 8.60 (s, 1H), 8.42 (m, 2H), 8.13 (d, J=8.8 Hz, 1H), 7.99 (d, J=2.2 Hz, 1H), 7.95 (s, 1H), 7.90 (s, 1H), 7.85 (d, J=8.0 Hz, 1H), 7.42 (s, 1H), 7.33 (t, J=7.3 Hz, 1H), 7.18 (t, J=7.1 Hz, 1H), 4.78 (s, 1H), 4.00 (s, 3H), 3.92 (br s, 2H), 3.63 (m, 2H), 3.11 (s, 3H), 2.95 (d, J=11.0 Hz, 2H), 1.97 (m, 2H), 1.07 (d, J=6.4 Hz, 6H)

Hemi Naphthalenedisulfonate Salt

Isopropylacetate (12 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.2 g) followed by naphthalenedisulfonic acid (0.0703 g) in isopropylacetate (2 ml). The suspension was stirred at ambient temperature for 9 days prior to filtration and dried under vacuum at 40° C. for 3 hrs to give the hemi napthalenedisulfonate.

NMR Consistent with Hemi Naphthalenedisulfonate Formation $^1$H NMR (400 MHz, DMSO d6) d=13.56 (br s, 1H), 10.38 (br s, 1H), 9.42 (s, 1H), 8.85 (d, J=8.8 Hz, 1H), 8.69 (s, 1H), 8.43 (d, J=2.5, 1H), 8.03 (s, 1H), 7.99 (d, J=2.2 Hz, 1H), 7.96 (s, 1H), 7.93 (d, J=7.1 Hz, 1H), 7.69 (br s, 1H), 7.40 (t, J=7.8 Hz, 1H), 4.68 (br s, 2H), 4.00 (s, 3H), 3.80 (br s, 2H), 3.50 (br s, 2H), 3.11 (s, 3H), 2.80 (br s, 2H), 1.15 (d, J=6.1 Hz, 6H)

Integrals at 4.68 and 2.80 are only at 1.6H not the expected 2H

Extra peaks due to ca. 0.1 eq isopropylacetate.

Raman: Not consistent with freebase forms known

Mesitylenesulfonate Salt

A solution of mesitylenesulfonic acid dihydrate (0.0698 g, 0.295 mmol, 1.0 eq) in tetrahydrofuran (0.5 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.1505 g, 0.294 mmol) and sonicated to give a clear solution. After stirring at ambient temperature for ca. 2 mins the solution had formed a very thick suspension. This was held at ambient temperature overnight. The solids were collected by filtration and washed with tetrahydrofuran (1-2 ml) before being dried in vacuo at 50° C. overnight to give the mesitylenesulfonate salt (0.1399 g, 66.8% th).

NMR: consistent with salt formation $^1$H NMR (400 MHz, DMSO d6) d=13.56 (s, 1H), 10.39 (bs, 1H), 9.42 (s, 1H), 8.69 (s, 1H), 8.43 (d, J=2.2 Hz, 1H), 8.03 (s, 1H), 7.99 (d, J=2.2 Hz, 1H), 7.96 (s, 1H), 7.69 (s, 1H), 6.73 (s, 2H), 4.69 (bs, 2H), 4.01 (s, 3H), 3.81 (bs, 2H), 3.49 (bs, 4H), 3.11 (s, 3H), 2.79 (bs, 2H), 2.16 (s, 3H), 1.15 (d, J=6.1 Hz, 6H).

Two methyl groups from mesitylenesulfonic acid are not seen as they overlap with resonance from d$_5$H-DMSO.

Hemi Biphenyldisulfonate

A solution of biphenyldisulfonic acid (0.0465 g, 0.148 mmol, 0.5 eq) in tetrahydrofuran (0.2 ml) and water (0.2 ml) was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.1506 g, 0.294 mmol) and sonicated to give a solution which was stirred at ambient temperature overnight. After this time the solution set solid due to a precipitate. These solids were collected by filtration and washed with tetrahydrofuran (1-2 ml) before being dried in vacuo at 50° C. overnight to give the hemi-biphenyldisulfonate salt (0.117 g, 59.5% th)

NMR: consistent with salt formation $^1$H NMR (400 MHz, DMSO d6) d=13.55 (s, 1H), 10.37 (bs, 1H), 9.42 (s, 1H), 8.69 (s, 1H), 8.43 (d, J=2.2 Hz, 1H), 8.03 (s, 1H), 7.99 (d, J=2.2 Hz, 1H), 7.96 (s, 1H), 7.66 (s+d, J=8.1 Hz, 1H+2H), 7.61 (d, J=8.3 Hz, 2H), 4.69 (bs, 2H), 4.01 (s, 3H), 3.81 (bs, 2H), 3.50 (bs, 4H), 3.11 (s, 3H), 2.79 (bs, 2H), 1.16 (d, J=6.1 Hz, 6H).

2-Naphthalenesulfonate (Napsylate)

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (0.200 g, 0.390 mmol) was dissolved in tetrahydrofuran (3.2 ml) and water (0.8 ml). Separately, 2-naphthalenesulfonic acid (0.081 mg, 0.390 mmol, 1.0 eq) was dissolved in tetrahydrofuran (0.8 ml) and added to the N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide solution. This was seeded with a previous napsylate salt, however these seeds dissolved. The solution was allowed to evaporate at ambient temperature for 2 days. The white solid formed was triturated in water and sonicated before being filtered and washed with water. The damp solids were dried further in vacuo at 40-50° C. for 5 days to give the napsylate salt (254.8 mg, 91% th).

NMR: consistent with salt formation

NMR (400 MHz, DMSO d6) d=13.56 (s, 1H), 10.38 (bs, 1H), 9.42 (s, 1H), 8.69 (s, 1H), 8.43 (d, J=2.2 Hz, 1H), 8.15 (s, 1H), 8.03 (s, 1H), 8.00 (d, J=2.0 Hz, 1H), 7.96 (m, 2H), 7.86 (m, 2H), 7.71 (m, 2H), 7.53 (m, 2H), 4.68 (bs, 2H), 4.01 (s, 3H), 3.79 (bs, 2H), 3.50 (bs, 2H), 3.11 (s, 3H), 2.78 (bs, 2H), 1.14 (d, J=6.1 Hz, 6H).

NMR also shows some unidentified low level impurities and residual tetrahydrofuran (0.1 molar equivalents).

Hemi Cinnamate

Method A

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (0.02505 g, 0.049 mmol) was treated with trans-cinnamic acid (0.01453 g, 0.098 mmol, 2.0 eq) in methanol (0.5 ml). This was heated with a hot air gun until dissolution occurred then allowed to cool to room temperature.

Solids precipitated on returning to room temperature and were allowed to stir overnight. The solids were filtered and solvent removed by pulling vacuum through the cake to give the salt.

Method B

N-[5-[4-(5-{[(2R,6S)-2,6-Dimethyl-4-morpholinyl]methyl}-1,3-oxazol-2-yl)-1H-indazol-6-yl]-2-(methyloxy)-3-pyridinyl]methanesulfonamide (80 g, 0.156 mol) and trans-cinnamic acid (58.66 g, 0.396 mol, 2.5 eq) were dissolved in methanol (3.2 L) by heating to 65° C. The solution was cooled to 60° C. and seeded with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide hemi-cinnamate (0.0802 g), these dissolved so the solution was cooled further to 50° C. and reseeded with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide hemi-cinnamate. This was stirred for 1 hr at 50° C. and then cooled at −0.167° C./min to 20° C. After 2 hrs a sample was taken and proved to be Form 3 by Raman analysis. The slurry was heated back to reflux to give a solution and extra methanol (100 ml) was added to make up for solvent losses incurred during the extended high temperature process. The solution was cooled to 25° C. and sample taken which was seeded with N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide hemi-cinnamate. This seeded sample was aged for 20 mins and then used to seed the bulk solution. This was allowed to stir at 25° C. for 16 hrs. The slurry was filtered and sucked dry before being dried in vacuo at 50° C. to give the salt (75.4 g, 82.5% th).

NMR: consistent with salt formation

NMR (400 MHz, DMSO d6) d=13.49 (bs, 1H), 9.40 (bs, 1H), 8.58 (s, 1H), 8.42 (d, J=2.5 Hz, 1H), 7.99 (d, J=2.2 Hz, 1H), 7.94 (s, 1H), 7.88 (s, 1H), 7.68 (m, 1H), 7.57 (d, J=16.1 Hz, 0.5H), 7.42 (m, 1.5H), 7.35 (s, 1H), 6.55 (d, J=15.9 Hz, 0.5H), 4.01 (s, 3H), 3.74 (s, 2H), 3.58 (m, 2H), 3.12 (s, 3H), 2.80 (d, J=10.5, 2H), 1.78 (t, J=10.5, 2H), 1.05 (d, J=6.1 Hz, 6H).

NMR also shows residual methanol (signal 3.18 ppm) at <0.1 molar equivalents.

Hemi Sebacate

A solution of sebacic acid (118.6 mg, 0.586 mmol, 2.0 eq) in THF (2 ml) was made up and added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (150.6 mg, 0.294 mmol) and heated to give a clear solution. The solution was allowed to cool to room temperature with stirring and after 2 hrs solids were present. A further aliquot of THF was added at this point and the suspension stirred overnight at ambient temperature. The solids were isolated by filtration and dried in vacuo at 50° C. overnight to give the hemi-sebacate salt.

NMR: consistent with salt formation

NMR (400 MHz, DMSO d6) d=13.49 (s, 1H), 11.94 (bs, 1H), 10.38 (bs, 1H), 9.38 (s, 1H), 8.58 (s, 1H), 8.42 (d, J=2.2 Hz, 1H), 7.99 (d, J=2.0 Hz, 1H), 7.93 (s, 1H), 7.88 (s, 1H), 7.35 (s, 1H), 4.00 (s, 3H), 3.74 (s, 2H), 3.11 (s, 3H), 2.80 (d, J=10.5, 2H), 2.18 (t, J=7.3 Hz, 2H), 1.48 (t, J=6.8 Hz, 2H), 1.25 (s, 4H), 1.05 (d, J=6.1 Hz, 6H).

Sample contains 0.85 molar equivalents tetrahydrofuran—NMR signals 3.60 ppm (m, 3.3H) and 1.76 ppm (m, 3.4H).

Hemi Pyromellitate

A solution of pyromellitic acid (0.0546 g, 0.215 mmol, 0.55 eq) was made up in tetrahydrofuran (1 ml) and added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.1999 g, 0.390 mmol) followed by further tetrahydrofuran (1 ml). This suspension was sonicated at which point the solids changed physical character and set solid. A further aliquot of tetrahydrofuran (2 ml) was added and the solution was heated and sonicated, however dissolution was not observed. The suspension was allowed to cool and stir overnight at room temperature. The solids were collected by filtration and washed with tetrahydrofuran (2 ml) before drying in vacuo overnight at 50° C. to give the hemi-pyromellitate salt as a tetrahydrofuran solvate.

NMR: consistent with salt formation

NMR (400 MHz, DMSO d6) d=13.52 (s, 1H), 9.39 (s, 1H), 8.61 (s, 1H), 8.42 (d, J=2.2 Hz, 1H), 8.20 (s, 1H), 7.99 (d, J=2.2 Hz, 1H), 7.96 (s, 1H), 7.91 (s, 1H), 7.45 (s, 1H), 4.01 (s, 5H), 3.60 (m, 6H), 3.11 (s, 3H), 3.02 (d, J=10.8 Hz, 2H), 2.06 (bs, 2H), 1.76 (m, 4H), 1.05 (d, J=6.1 Hz, 6H).

Tetrahydrofuran signals are 3.60 ppm (m, 4H) and 1.76 ppm (M, 4H) corresponding to 1 molar equivalent.

Hemi Benzenediacrylate 1,4-Benzenediacrylic acid (0.0431 g, 0.197 mmol, 0.5 eq) was dissolved in dimethylsulfoxide (0.5 ml) with heating, this was added to N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide (0.2003 g, 0.391 mmol) and heated to give a solution. Tetrahydrofuran (1 ml) was added to the solution and it was then heated and sonicated before being allowed to stir at room temperature overnight. The solids were isolated by filtration and washed with tetrahydrofuran before being dried in vacuo at 65° C. overnight to give the hemi-benzenediacrylate salt (0.1385 g, 57% th).

NMR: consistent with salt formation

NMR (400 MHz, DMSO d6) d=13.49 (bs, 1H), 12.40 (bs, 1H), 9.38 (bs, 1H), 8.58 (s, 1H), 8.42 (d, J=2.2 Hz, 1H), 7.99 (d, J=2.2 Hz, 1H), 7.93 (s, 1H), 7.88 (s, 1H), 7.73 (s, 2H), 7.58 (d, J=16.1 Hz, 1H), 7.35 (s, 1H), 6.62 (d, J=16.1 Hz, 1H), 4.00 (s, 3H), 3.74 (s, 2H), 3.11 (s, 3H), 2.80 (d, J=10.5 Hz, 2H), 1.05 (d, J=6.4 Hz, 6H). Tetrahydrofuran signals are 3.60 ppm (m, 2.7H) and 1.78 ppm (m, 2.7H) corresponding to 0.68 molar equivalent. Dimethylsulfoxide signal is 2.54 ppm (s, 0.7H) corresponding to 0.12 molar equivalents.

What is claimed is:

1. A polymorph (Form III) of N-[5-[4-(5-{[(2R,6S)-2,6-dimethyl-4-morpholinyl]methyl}-1,3-oxazol-2-yl)-1H-indazol-6-yl]-2-(methyloxy) 3-pyridinyl]methanesulfonamide characterised in that it provides an XRPD pattern comprising peaks (°2θ) at about 6.7, about 8.2, about 9.7 and/or about 12.6.

2. A polymorph according to claim 1 characterised in that it provides an XRPD pattern comprising peaks substantially as set out in Table 2.

3. A polymorph according to claim 1 characterised in that it provides an XRPD pattern substantially in accordance with FIG. 2.

* * * * *